United States Patent
Vladimirsky et al.

(10) Patent No.: US 8,634,054 B2
(45) Date of Patent: Jan. 21, 2014

(54) PARTICLE DETECTION ON AN OBJECT SURFACE

(75) Inventors: Yuli Vladimirsky, Weston, CT (US); James H. Walsh, Newtown, CT (US)

(73) Assignee: ASML Holding N.V., Veldhoven (NL)

(*) Notice: Subject to any disclaimer, the term of this patent is extended or adjusted under 35 U.S.C. 154(b) by 621 days.

(21) Appl. No.: 12/537,728

(22) Filed: Aug. 7, 2009

(65) Prior Publication Data
US 2010/0045955 A1  Feb. 25, 2010

Related U.S. Application Data

(60) Provisional application No. 61/090,437, filed on Aug. 20, 2008.

(51) Int. Cl.
| G01N 21/00 | (2006.01) |
| G03B 27/32 | (2006.01) |
| G03B 27/42 | (2006.01) |
| G03B 27/52 | (2006.01) |
| G03B 27/80 | (2006.01) |

(52) U.S. Cl.
USPC ............... 355/30; 355/53; 355/68; 355/77; 356/237.3; 356/237.4

(58) Field of Classification Search
USPC .......... 348/86–87; 355/30, 40–41, 53, 67–68, 355/70, 77; 356/237.2–237.5
See application file for complete search history.

(56) References Cited

U.S. PATENT DOCUMENTS

| 4,669,885 A | * | 6/1987 | Ina .................................. 356/443 |
| 5,581,348 A | * | 12/1996 | Miura et al. ................ 356/237.2 |
| 6,043,864 A | * | 3/2000 | Lo et al. .......................... 355/53 |
| 6,177,952 B1 | | 1/2001 | Tabata et al. |
| 2007/0081135 A1 | * | 4/2007 | Kamono ......................... 355/53 |
| 2008/0259319 A1 | * | 10/2008 | Mitome .......................... 356/73 |
| 2011/0279805 A1 | * | 11/2011 | Ryzhikov et al. .............. 355/72 |

FOREIGN PATENT DOCUMENTS

| JP | 07043312 A | * | 2/1995 |
| JP | 7-095622 A | | 4/1995 |
| JP | 10-221267 A | | 8/1998 |
| JP | 2002-228428 A | | 8/2002 |
| JP | 2002-340537 A | | 11/2002 |
| JP | 2006-029955 A | | 2/2006 |

OTHER PUBLICATIONS

English-Language Abstract for JP 7-095622 A, published Apr. 7, 1995; 1 page.
English-Language Abstract for JP 2002-340537 A, published Nov. 27, 2002; 1 page.

(Continued)

*Primary Examiner* — Toan Ton
*Assistant Examiner* — Colin Kreutzer
(74) *Attorney, Agent, or Firm* — Sterne, Kessler, Goldstein & Fox P.L.L.C

(57) ABSTRACT

Systems and methods are provided for inspecting an object surface. An illumination source illuminates the object surface. An optic intercepts scattered light from the illuminated object surface and projects a real image of an area of the object surface. A sensor receives the projected real image. A computer system, coupled to the sensor, stores and analyzes the real image. The real image is processed to detect particles located on the object surface. This arrangement is particularly useful for detecting contaminants or defects on a reticle of a lithography device.

20 Claims, 27 Drawing Sheets

(56) References Cited

OTHER PUBLICATIONS

English-Language Abstract for JP 2006-029955 A, published Feb. 2, 2006; 1 page.

English-Language Translation of Non-Final Office Action directed to related Korean Patent Application No. 10-2009-0077071, mailed Jun. 20, 2011, from the Korean Intellectual Property Office; 4 pages.

* cited by examiner

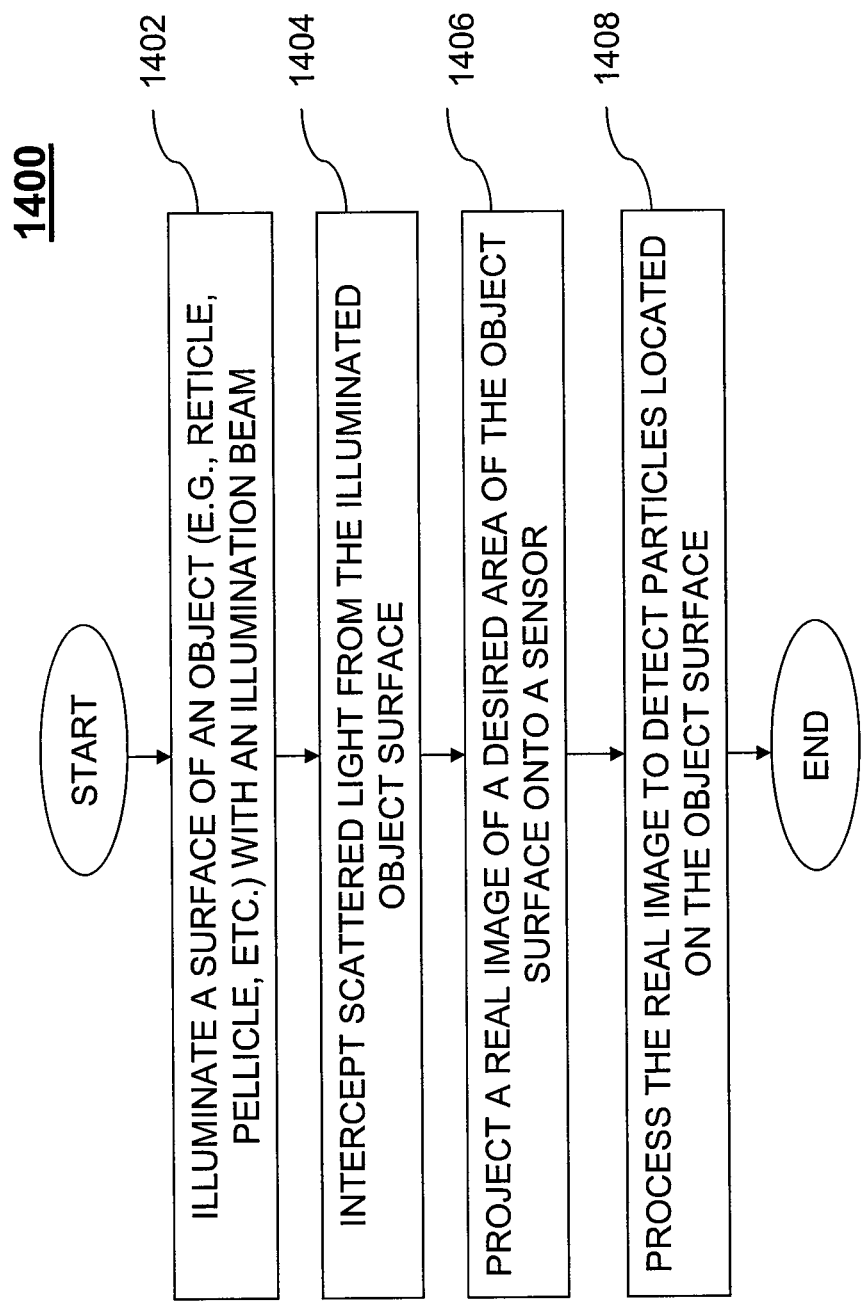

PARTICLE DETECTION ON AN OBJECT SURFACE

CROSS-REFERENCE TO RELATED APPLICATIONS

This application claims the benefit under 35 U.S.C. §119(e) to Provisional Patent Application No. 61/090,437 filed Aug. 20, 2008, which is incorporated by reference herein in its entirety.

BACKGROUND

1. Field of the Invention

The present invention generally relates to lithography, and more particularly to systems and methods for particle detection.

2. Related Art

Lithography is widely recognized as a key process in manufacturing integrated circuits (ICs) as well as other devices and/or structures. A lithographic apparatus is a machine, used during lithography, which applies a desired pattern onto a substrate, such as onto a target portion of the substrate. During manufacture of ICs with a lithographic apparatus, a patterning device (which is alternatively referred to as a mask or a reticle) generates a circuit pattern to be formed on an individual layer in an IC. This pattern may be transferred onto the target portion (e.g., comprising part of, one, or several dies) on the substrate (e.g., a silicon wafer). Transfer of the pattern is typically via imaging onto a layer of radiation-sensitive material (e.g., resist) provided on the substrate. In general, a single substrate contains a network of adjacent target portions that are successively patterned. Manufacturing different layers of the IC often requires imaging different patterns on different layers with different reticles. Therefore, reticles may be changed during the lithographic process.

Lithography systems project mask pattern features that are extremely small. Dust or extraneous particulate matter appearing on the surface of the reticle can adversely affect the resulting product. Any particulate matter that deposits on the reticle before or during a lithographic process is likely to distort features in the pattern being projected onto a substrate. Therefore, the smaller the feature size, the smaller the size of particles that it is critical to eliminate from the reticle.

A pellicle is often used with a reticle. A pellicle is a thin transparent layer that may be stretched over a frame above the surface of a reticle. Pellicles are used to block particles from reaching the patterned side of a reticle surface. Any particles on the pellicle surface are out of the focal plane and should not form an image on the wafer being exposed. However, it is still preferable to keep the pellicle surfaces as particle-free as possible.

In lithography, reticle inspection systems may be integrated with lithography tools. This integration can not only protect against printed defects caused by particles ranging from very small to very large, but can also detect crystallization on the reticle, allowing as-late-as-possible reticle cleaning, which can in turn increase machine throughput and utilization. Condition-based reticle cleaning also enables cleaning frequency reduction, which can extend the life of reticles.

Currently used high throughput lithography tools employ rapid in-situ reticle inspection devices to detect particulate contamination. Requirements of speed and a high signal-to-noise ratio have led to utilization of a probe imaging technique, a type of scatterometry, for this purpose. This technique is based on collecting scattered light from contamination and dust particles that have been illuminated in a reasonably small spot on the reticle surface. A reasonably sized spot (e.g., approximately 50 µm to 300 µm) is rastered, or scanned, over a test surface, collecting information from one spot at a time. For a 150 mm by 120 mm surface, this corresponds to an approximately 9 Mpixel image. The probe beam technique is demonstrated in FIGS. 1A-1C, 2, and 3. FIG. 1A depicts a portion 102 of an object, such as a reticle or pellicle. Probe beam spots 104 are shown, with arrow 106 showing the scan direction of a probe beam. A particle 108 is shown on one of probe beam spots 104.

When using the probe beam technique, detection of particles smaller than 100 µm requires intensity quasi-calibration to represent particle size. The size of a particle is commonly determined in terms of Latex-Sphere Equivalence using sets of 5, 10, 30, and 50 µm latex spheres for intensity calibration. For particles up to 50 µm, interpolation of the scattered light amount may be necessary, and for particles up to 100 µm, extrapolation of the scattered light amount may be necessary. As shown in FIG. 1B, when an assembly of small particles within an illumination spot (e.g., probe beam spot 104) is present, this assembly may be recorded as one particle size equivalent to an effective signal collected within a specified pixel 110. Furthermore, an assembly of unresolved small particles may be reported as a single large particle 112, as shown in FIG. 1C.

FIG. 2 shows an example of the scanning, or rastering, of a surface of an object 220 that occurs when using the probe beam technique. In this example, a probe beam spot 204 is scanned in direction 246 while object 220 moves in direction 248. Because object 220 is scanned one probe beam spot at a time, a full assessment of the surface of object 220 is not complete until the scans are all complete. Furthermore, if a pellicized reticle is being assessed, it becomes necessary to run two complete sequential scans in order to assess both the reticle surface and the pellicle surface.

Using the probe beam technique, reflected scattered light is sampled and converted into a grey level bitmap, which can then be mapped as shown in map 350 in FIG. 3. Map 350 shows reported particles 352 that are greater than a particular size (e.g., greater than 10 µm).

The ultimate spatial resolution of the probe beam technique is defined by the beam spot size and pixel size, determined in its turn by designated collection time multiplied by raster speed. Spatial resolution is approximately equal to the spot autocorrelation function, or approximately to a double beam spot size, which can be improved with elaborate image processing, allowing resolution close to the illumination spot size to be achieved. However, detection optics only collect the scattered light during the time allocated for single pixel exposure, and do not resolve the illumination spot. Despite low spatial resolution, sub-pixel sized bright particles can be detected due to a very good signal-to-noise ratio, but cannot be imaged.

The probe beam technique also requires very elaborate and bulky scanning mechanisms that necessitate low numerical aperture (NA) optics in both illumination and detection paths. Use of low numerical aperture optics in the detection path results in a large depth-of-focus (DoF). This leads to inadvertently imaging real structures and objects formed by optical cross-talk that are far from the intended plane of inspection. As a result, probe-based inspection systems fail to adequately recognize contamination particles and fail to discriminate them from optical cross-talk images. Therefore, precision, quality, and certainty of particle size detection is very often compromised when using the probe beam technique.

Requirements for increased scan speed and stability are now limiting the ability of techniques such as the probe beam technique to be effective. In addition, increased scan speed decreases signal-to-noise ratios, limiting the ability to differentiate small particles from noise. Furthermore, the probe beam technique is susceptible to optical cross-talk as line widths shrink. With increasing demands for higher throughput and shrinking lithographic feature sizes, it is becoming increasingly important to enhance a particle detection system's performance in terms of speed, smaller particle size detection, and immunity against unwanted effects such as optical cross-talk. Given the foregoing, what is needed are systems and methods for particle detection using true imaging.

BRIEF SUMMARY OF THE INVENTION

The purpose of this "summary" section is to summarize some aspects of the present invention and to briefly introduce some preferred embodiments. Simplifications or omissions may be made to avoid obscuring the purpose of the section. Such simplifications or omissions are not intended to limit the scope of the present invention. Consistent with the principles of the present invention as embodied and broadly described herein, the present invention is directed to particle detection on the surfaces of objects using true imaging, and applications thereof.

For example, an embodiment of the present invention provides a system for inspection of a surface of an object. In this system, there is at least one illumination source for providing an illumination beam to illuminate the surface of the object. In an embodiment, the illumination source or sources are configured such that the illumination beam is provided to the object surface at an oblique angle. The system also includes an optic for intercepting scattered light from the illuminated object surface and projecting a real image of a desired area of the object surface. The system further includes a sensor for receiving the projected real image. In an embodiment, the sensor can be placed to "look" at the object surface at an oblique angle, while the illumination beam can provide normal light. Particles located on the object surface are detectable in the real image. A computer system can be coupled to the sensor for storing and analyzing the real image.

Another embodiment of the present invention provides a method of detecting particles on a surface of an object. The method includes illuminating the surface of the object with an illumination beam. The method further includes intercepting scattered light from the illuminated object surface, and projecting a real image of a desired area of the object surface onto a sensor. The real image can then be processed to detect particles located on the object surface.

The above summarized system and method can be used for particle detection on objects such as a reticle and/or its associated pellicle of a lithography system while they are in place for actual use. As such, a further embodiment of the present invention provides a method of device manufacturing. This method includes assessing a surface of a reticle by producing a first illumination beam, illuminating the reticle surface with the first illumination beam, intercepting scattered light from the illuminated reticle surface, projecting a real image of a desired area of the reticle surface onto a sensor, and processing the real image to detect particles located on the reticle surface. Assessing a surface of the reticle's associated pellicle can be done in a similar manner. The method further includes producing a second illumination beam, illuminating the reticle with the second illumination beam, generating a pattern of the second illumination beam from the reticle, and projecting the patterned second illumination beam onto a target portion of a substrate.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

Figure 13A:
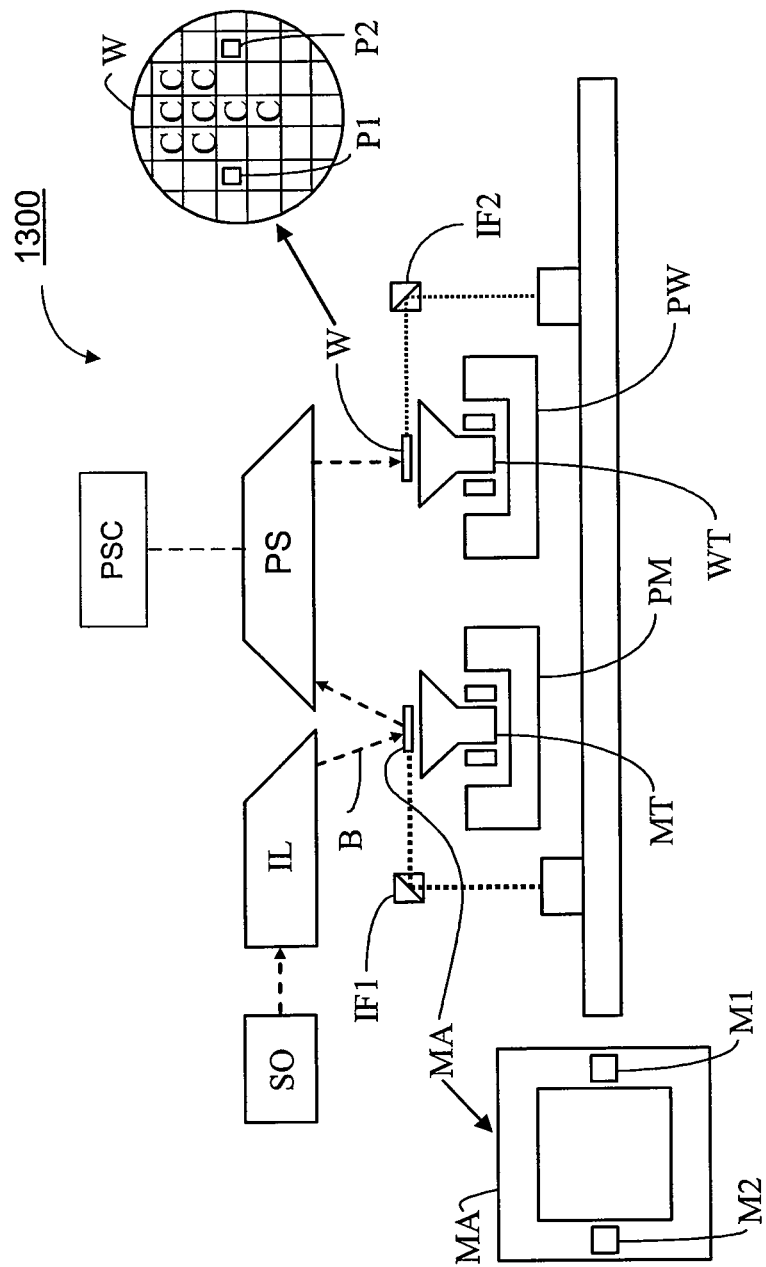
Figure 13B:
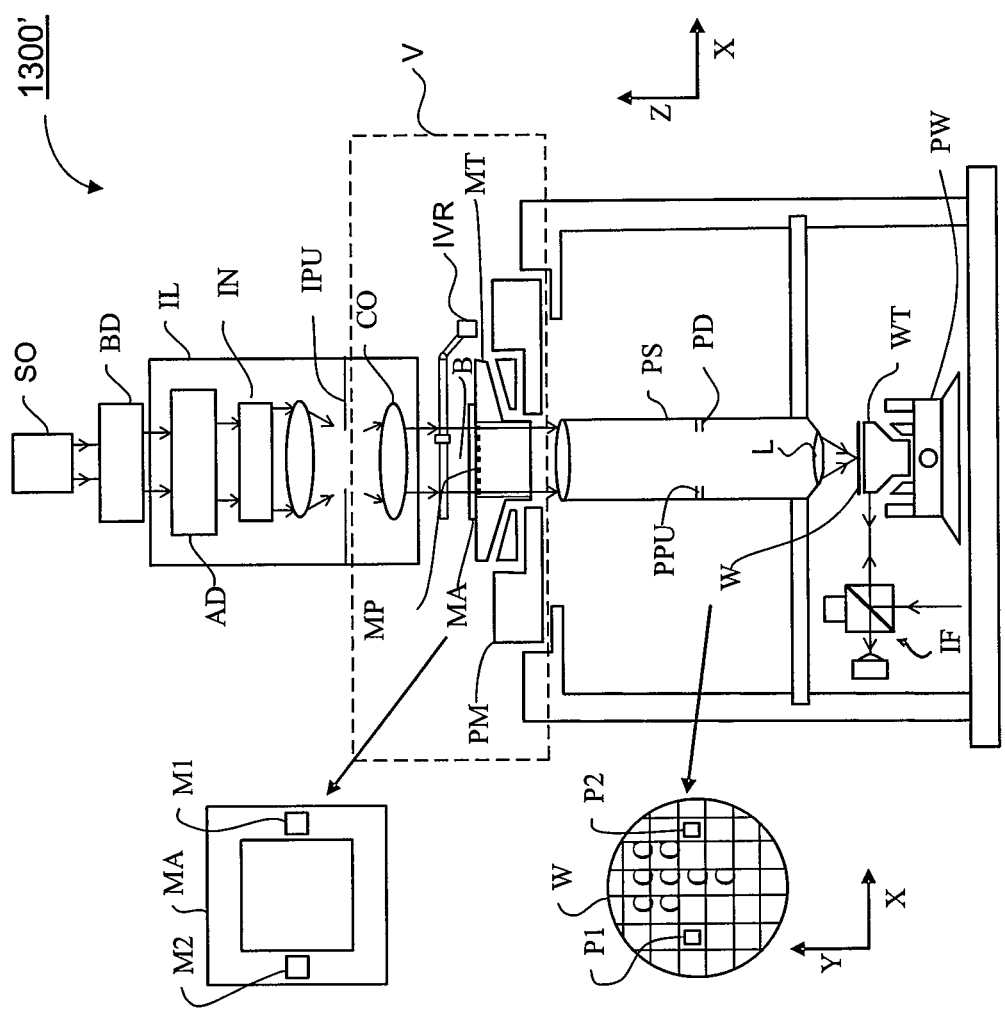

FIGS. 13A and 13B respectively depict exemplary reflective and transmissive lithographic apparatuses in which embodiments of the present invention can be used.

FIG. 14 depicts a flow diagram illustrating an example method for inspecting a surface of an object, according to an embodiment of the present invention.

Figure 15:
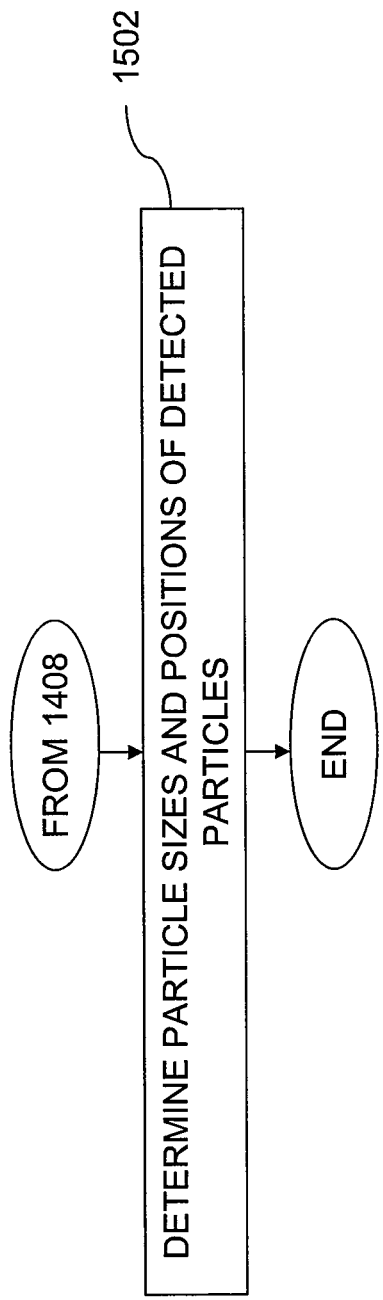
Figure 16:
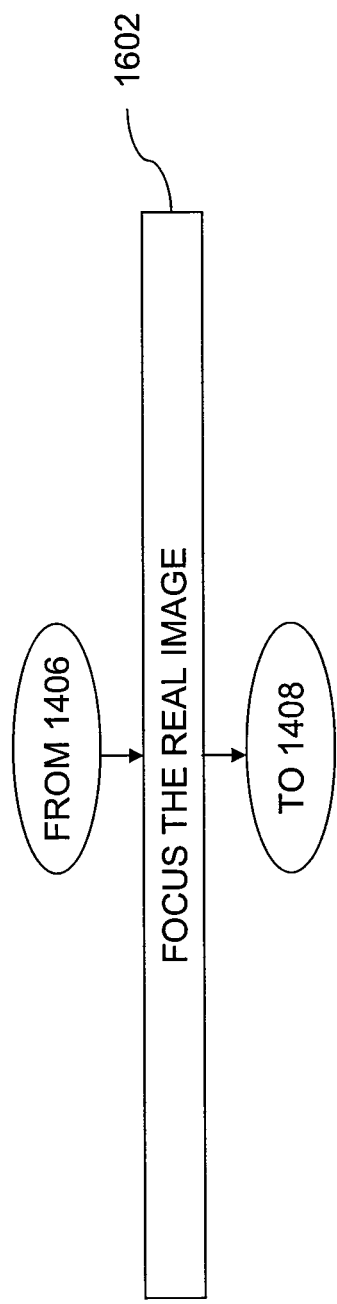

FIGS. 15 and 16 depict further optional steps of the method shown in FIG. 14, according to embodiments of the present invention.

Figure 17:
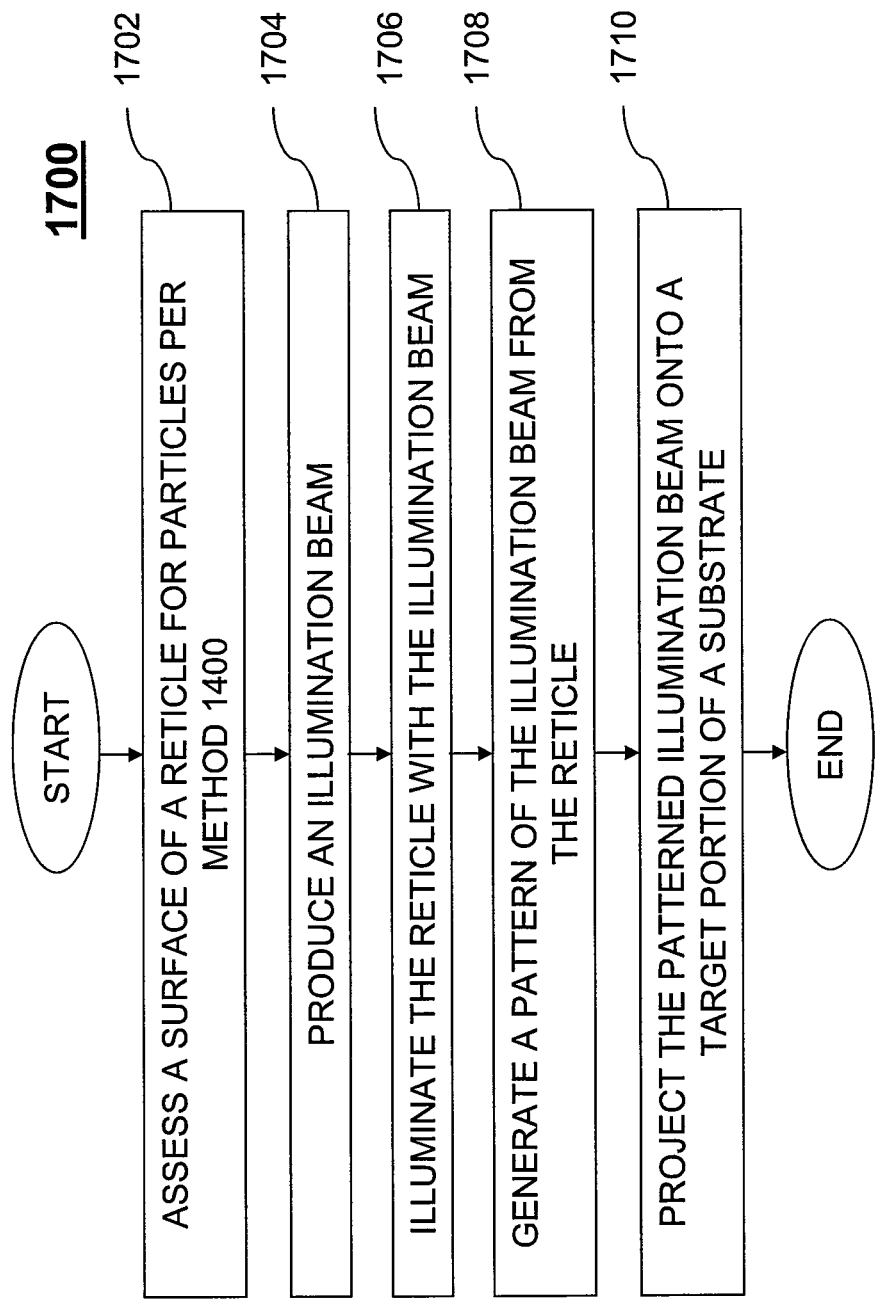

FIG. 17 depicts a flow diagram illustrating an example method for manufacturing a device, according to an embodiment of the present invention.

Figure 18:
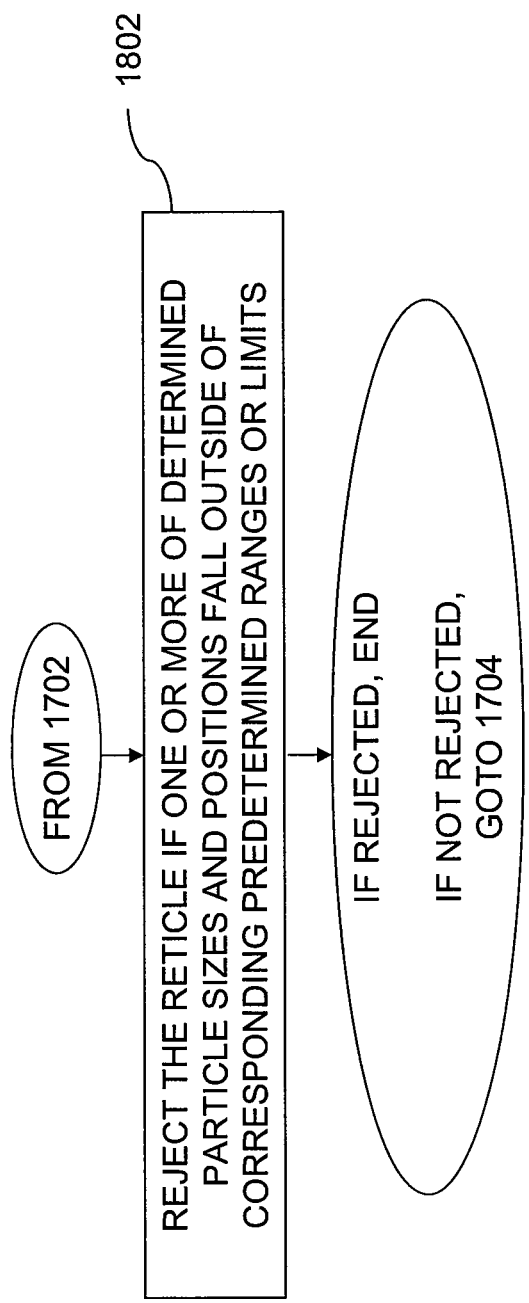
Figure 19:
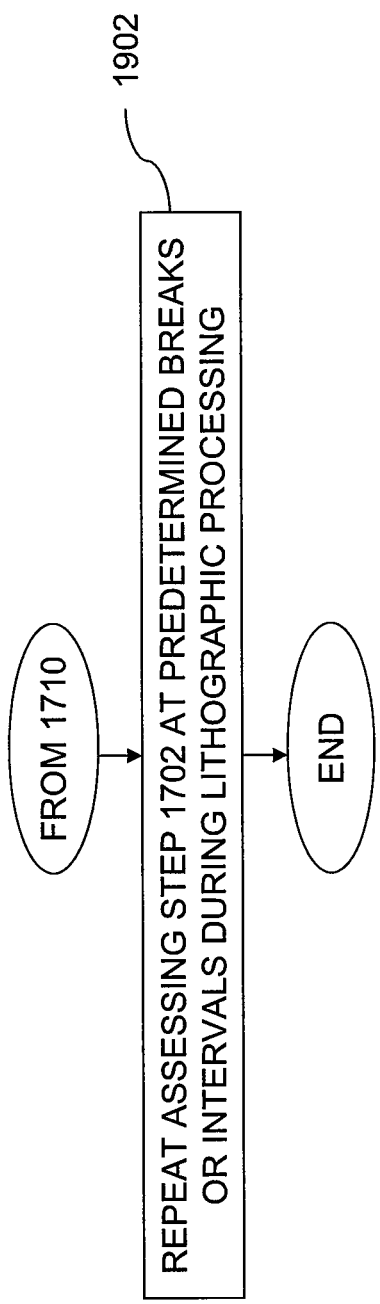

FIGS. 18 and 19 depict further optional steps of the method shown in FIG. 17, according to embodiments of the present invention.

Figure 20:
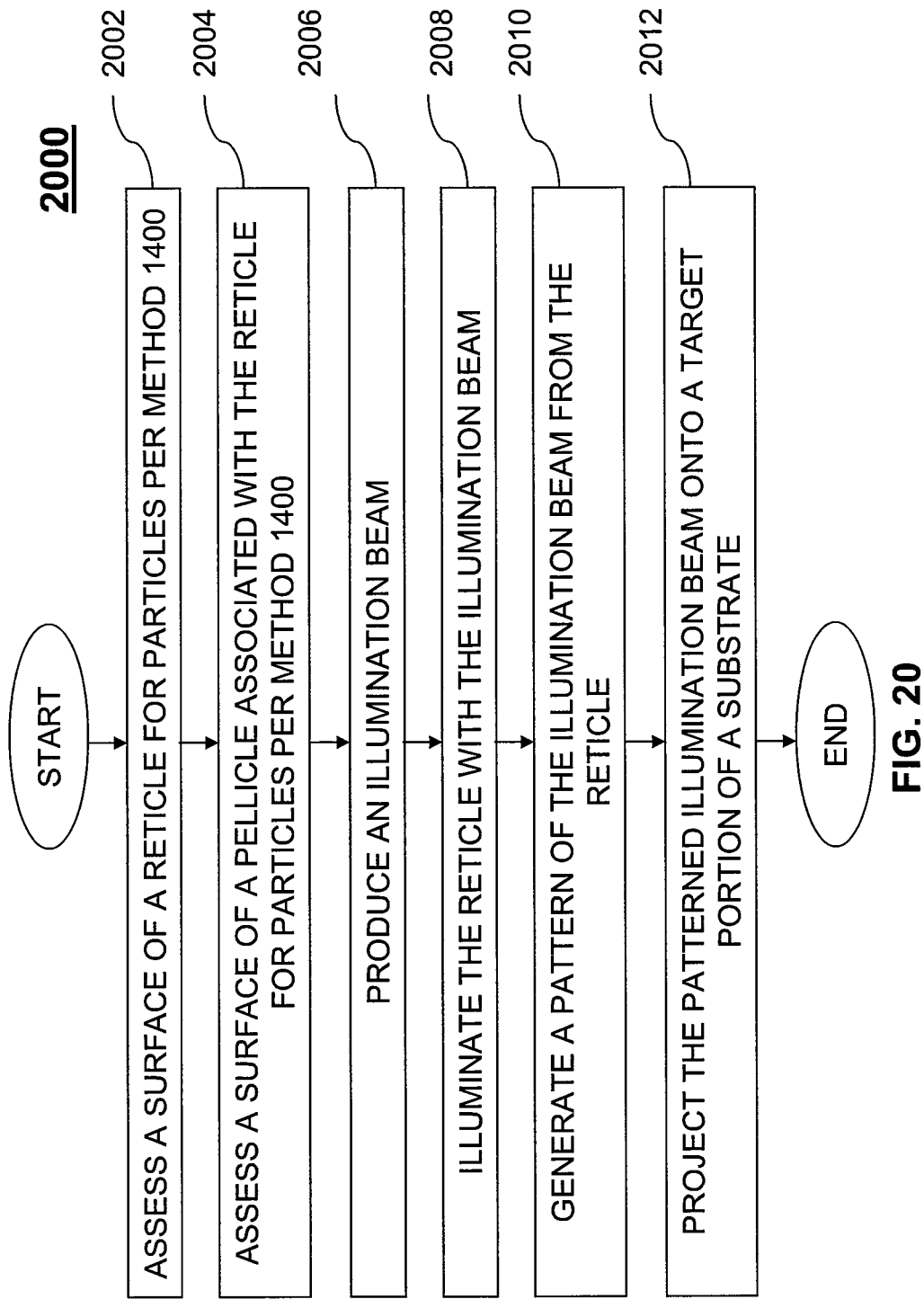

FIG. 20 depicts a flow diagram illustrating an example method for manufacturing a device, according to an embodiment of the present invention.

Figure 21:
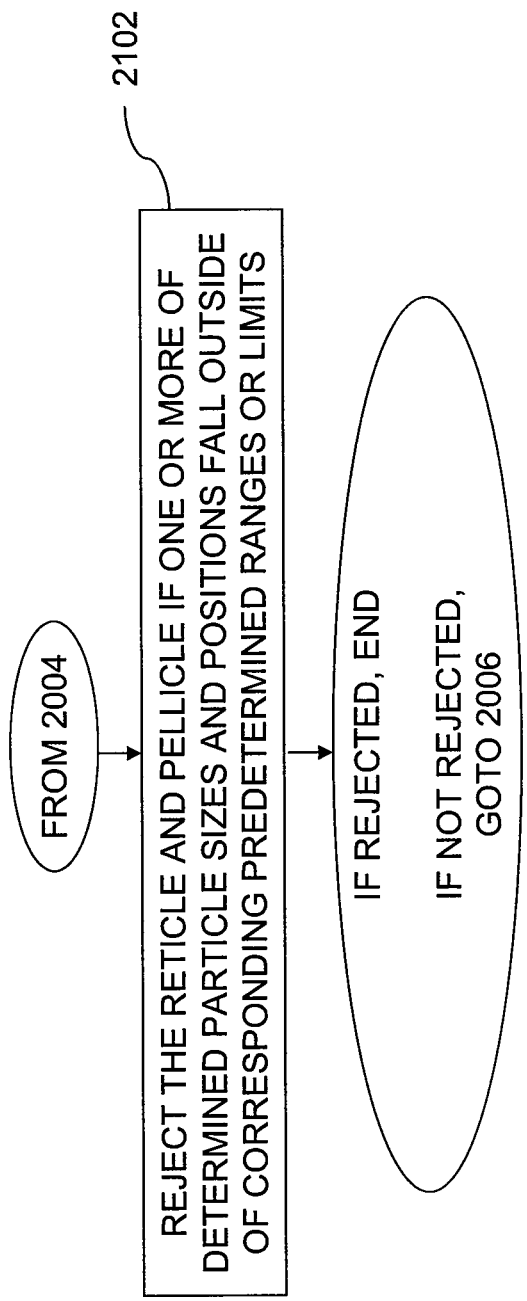
Figure 22:
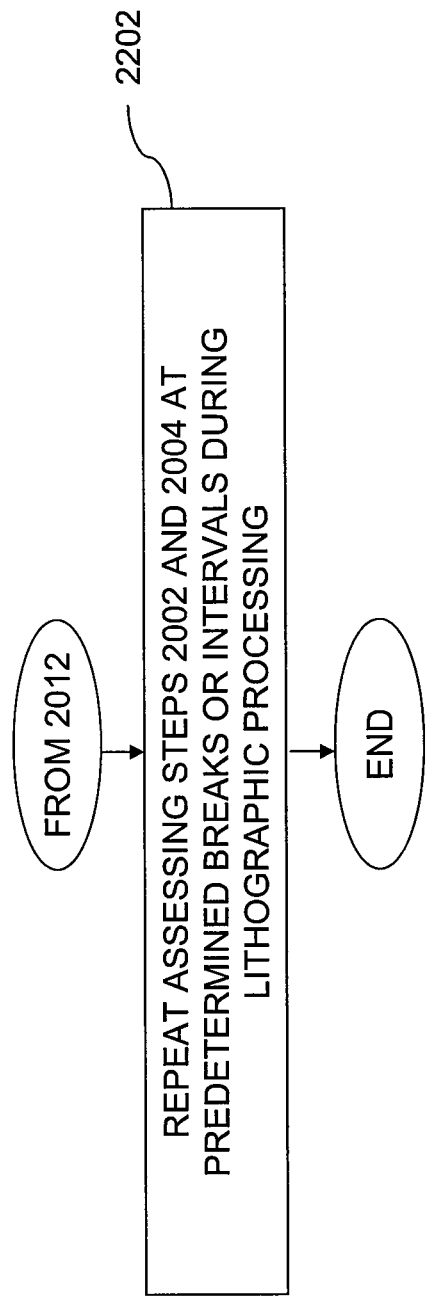
Figure 23:
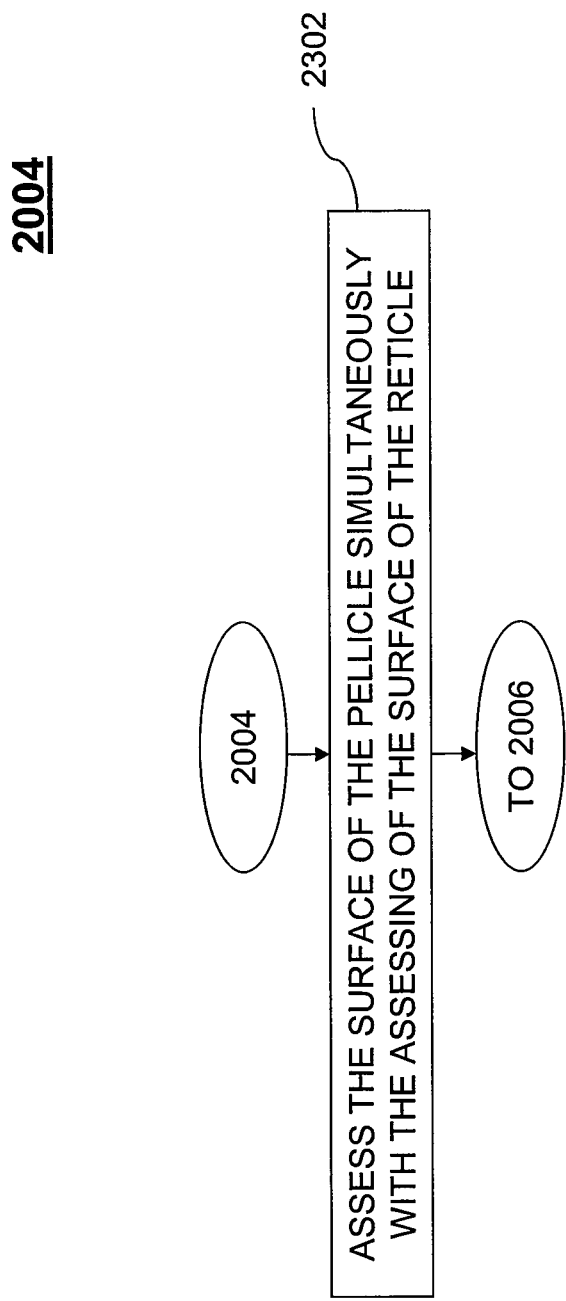

FIGS. 21-23 depict further optional steps of the method shown in FIG. 20, according to embodiments of the present invention.

Figure 24:
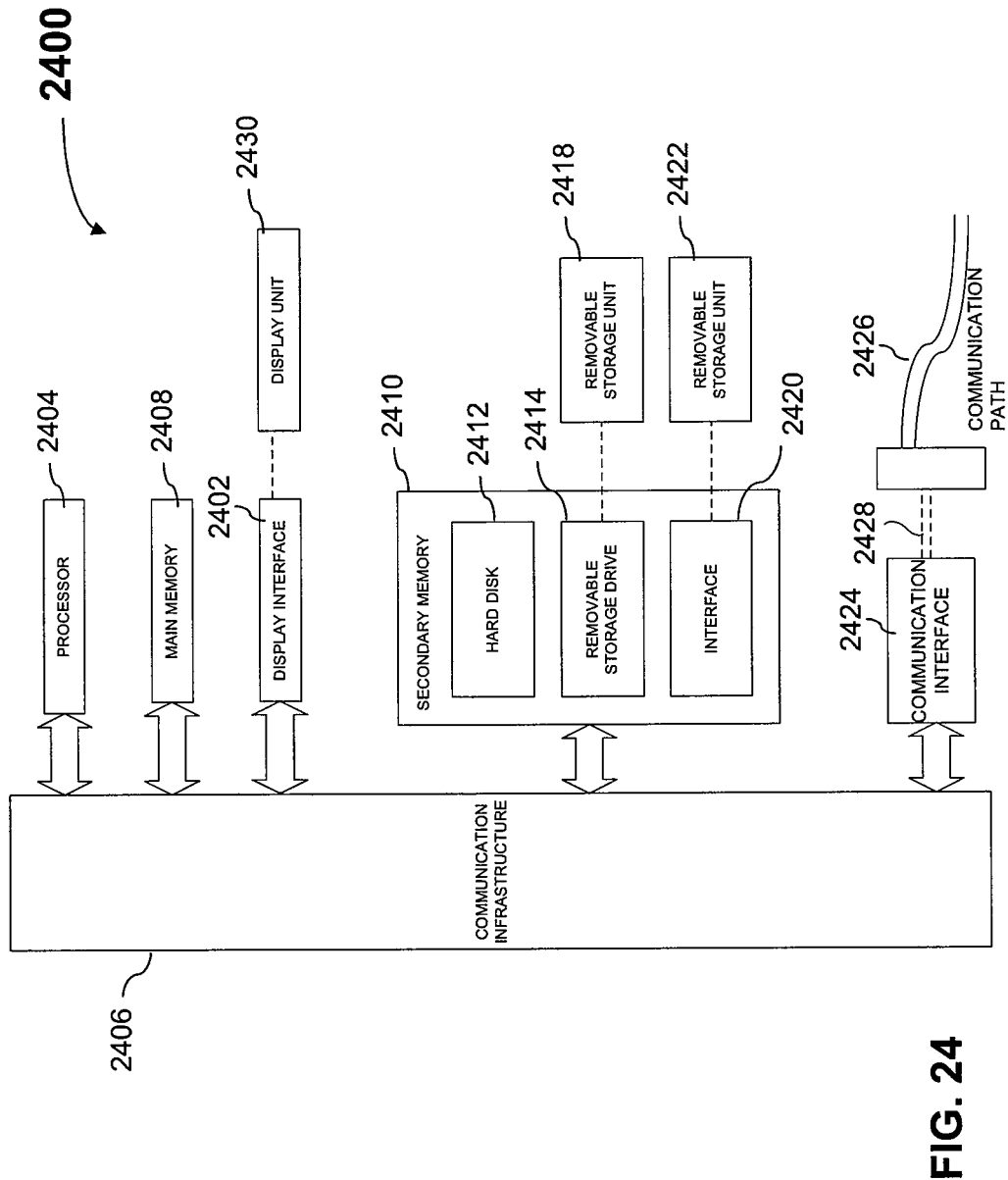

FIG. 24 depicts an example computer system that can be used to implement features and embodiments of the present invention.

Features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

I. Introduction

The invention will be better understood from the following descriptions of various "embodiments" of the invention. Thus, specific "embodiments" are views of the invention, but each does not itself represent the whole invention. In many cases individual elements from one particular embodiment may be substituted for different elements in another embodiment carrying out a similar or corresponding function. The present invention relates to particle detection on the surfaces of objects, and applications thereof. In the detailed description that follows, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Embodiments of the present invention are directed to particle detection on the surface of an object. Embodiments of this invention are based on true imaging and involve the acquisition of complete two-dimensional images of the surface to be assessed. New developments in machine vision technologies, and in particular large scale linear and area charge-coupled devices (CCDs), make it possible and viable to sample surfaces with high resolution in a true imaging mode. Embodiments of the invention will be particularly useful for in-situ reticle inspection systems for use in the lithography industry, for example. In lithography systems, embodiments of this invention are envisioned to be particularly useful for examining the non-patterned surfaces of a reticle and its associated pellicle. However, it can be appreciated that embodiments of the invention could also be used to assess either patterned or non-patterned surfaces of reticles, pellicles, and potentially other objects such as wafers.

II. Example Surface Inspection Systems

Figures 1A, 1B, 1C:
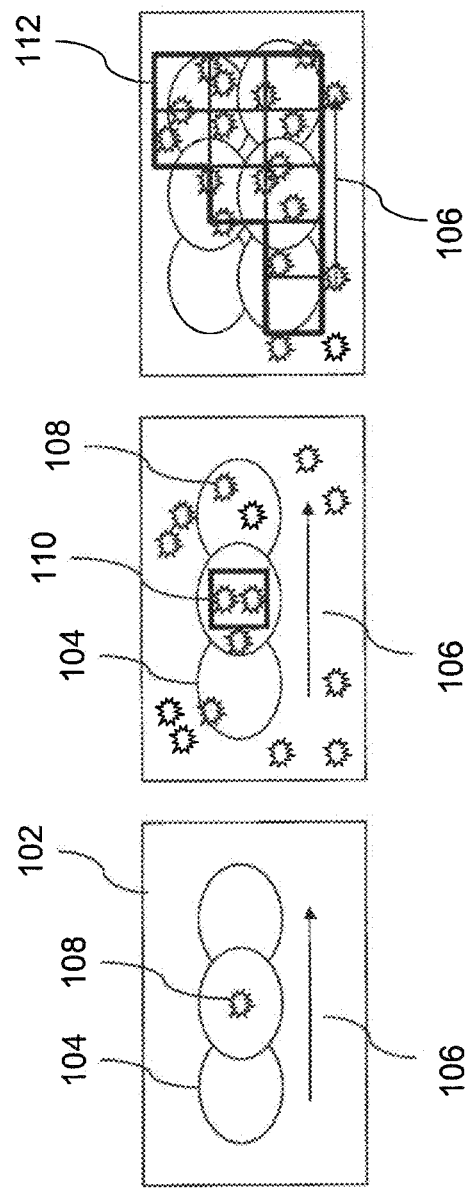
FIGS. 1A-1C depict examples of a probe beam technique of particle detection.
Figure 2:
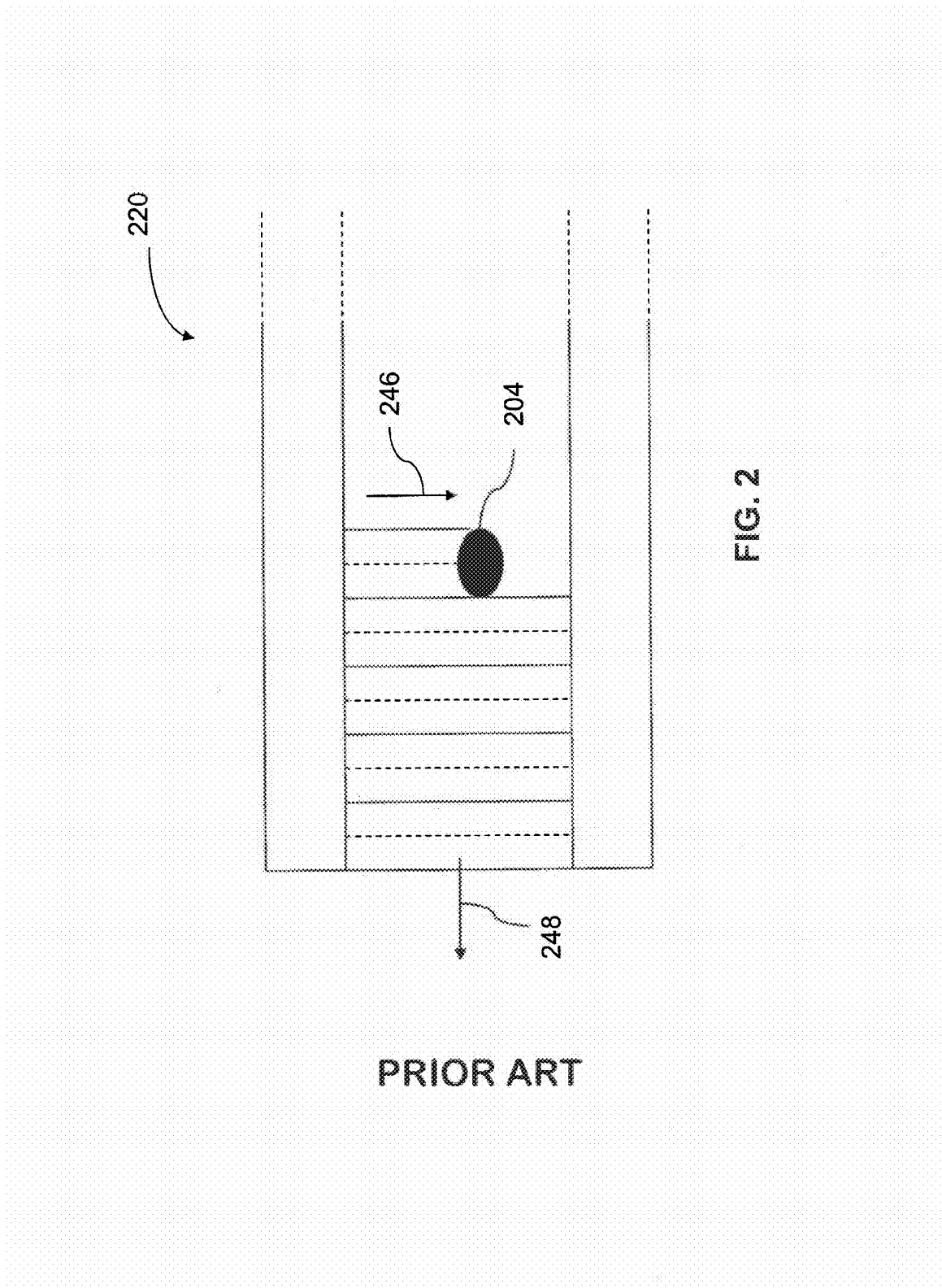
FIG. 2 depicts an example of scanning a surface using the probe beam technique.
Figure 3:
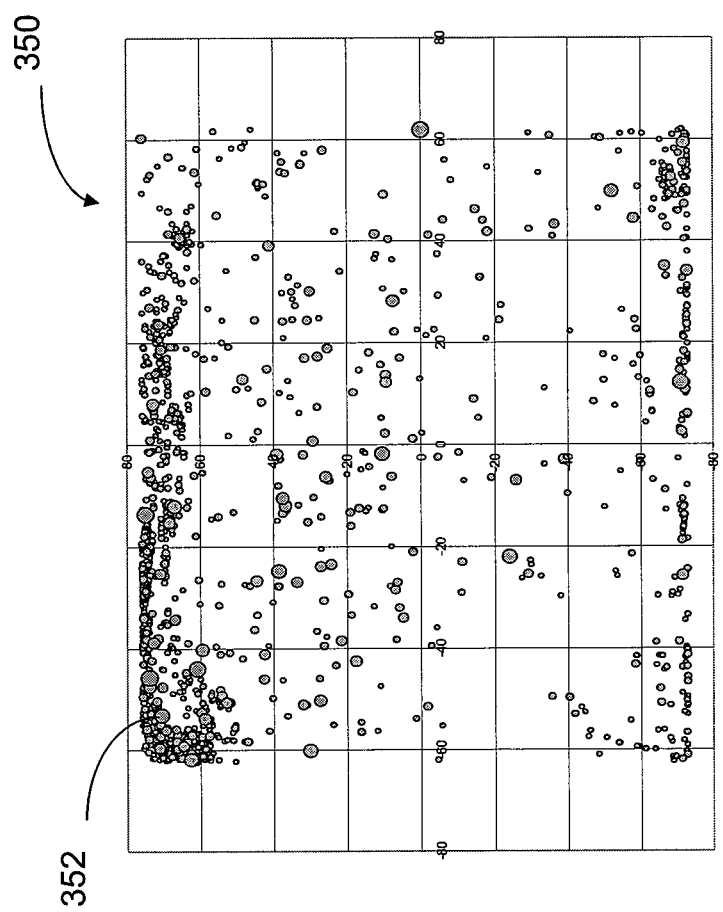
FIG. 3 depicts a map of reported particles found using the probe beam technique.
Figure 4:
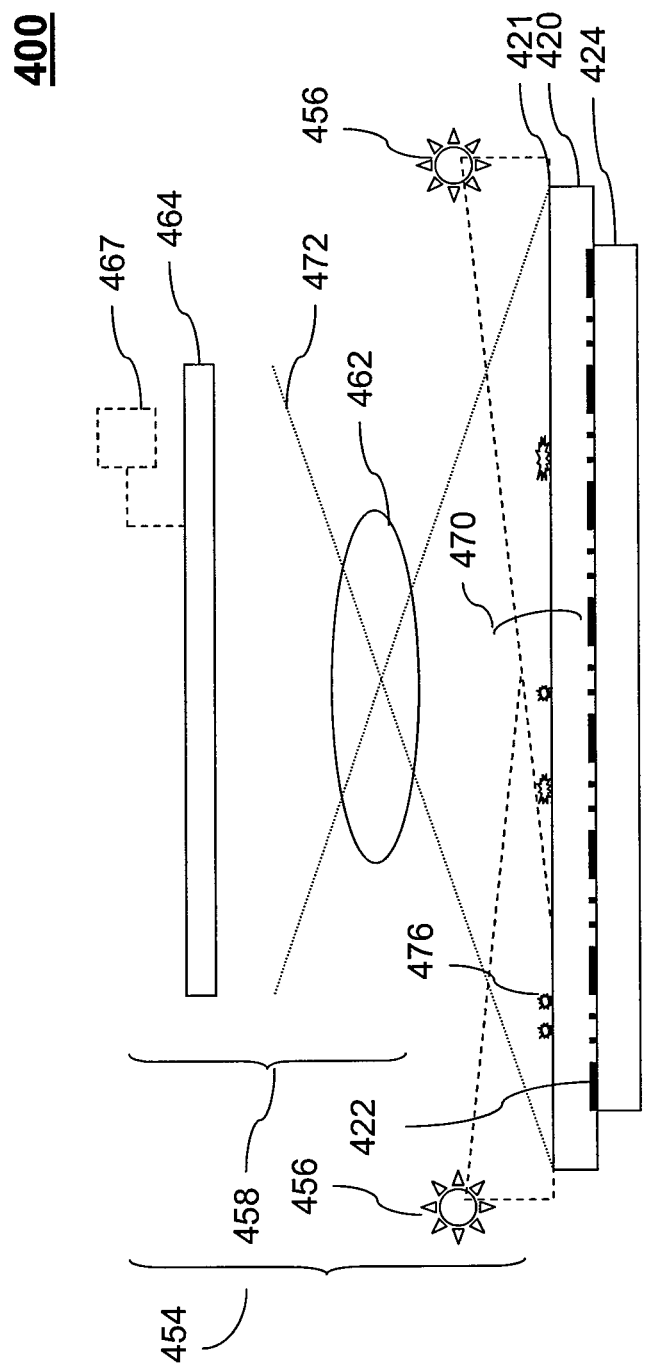
FIG. 4 illustrates a system for inspection of a surface of an object, according to an embodiment of the present invention.
Figure 6A:
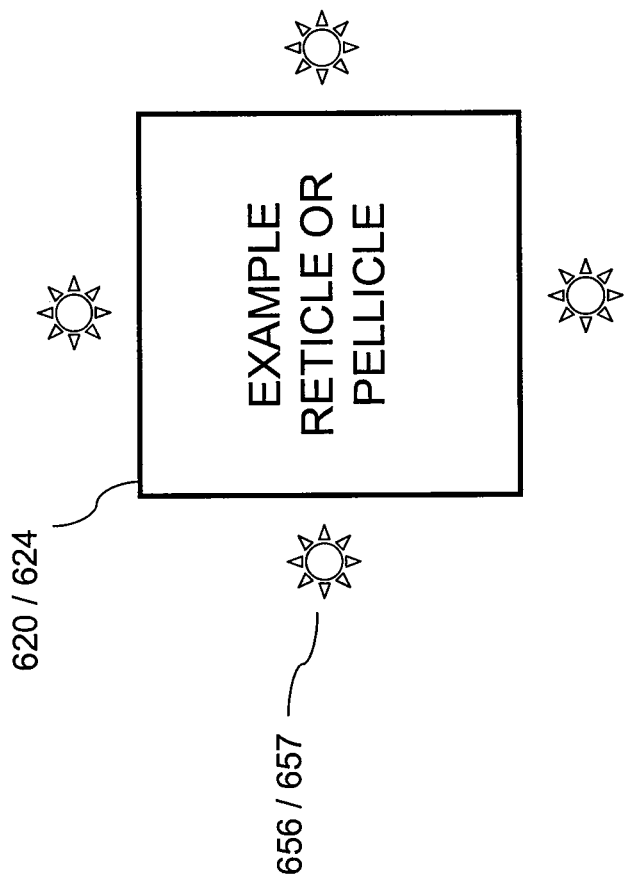
FIG. 6A illustrates usage of four illumination sources as could be used with the systems shown in FIGS. 4 and 5, according to an embodiment of the present invention.
Figure 6B:
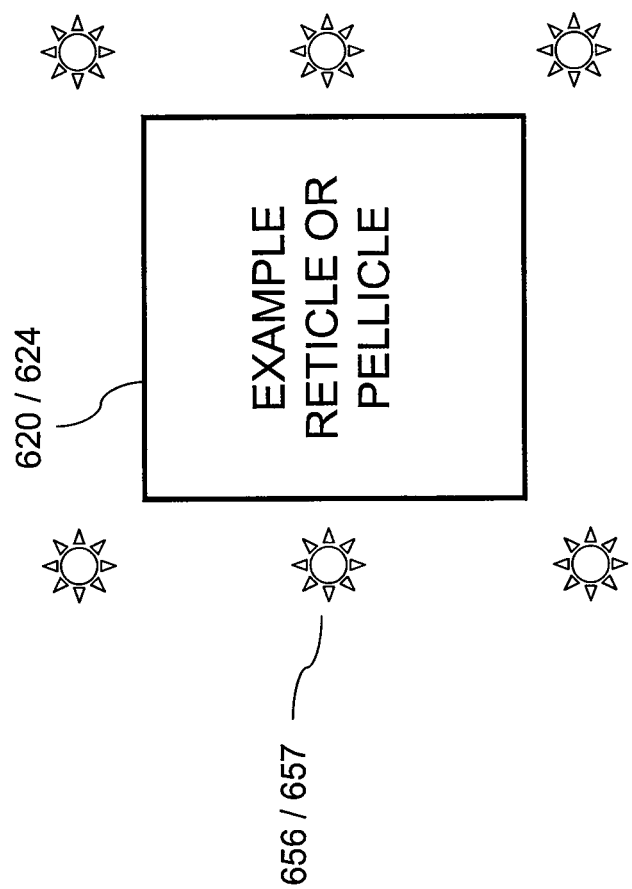
FIG. 6B illustrates usage of six illumination sources as could be used with the systems shown in FIGS. 4 and 5, according to an embodiment of the present invention.
Figure 6C:
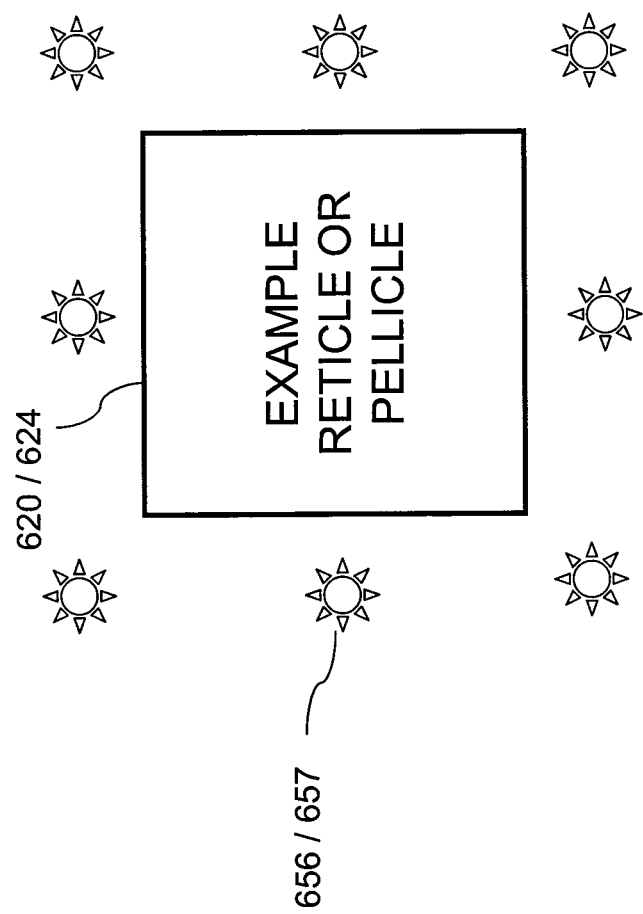
FIG. 6C illustrates usage of eight illumination sources as could be used with the systems shown in FIGS. 4 and 5, according to an embodiment of the present invention.
Figure 7:
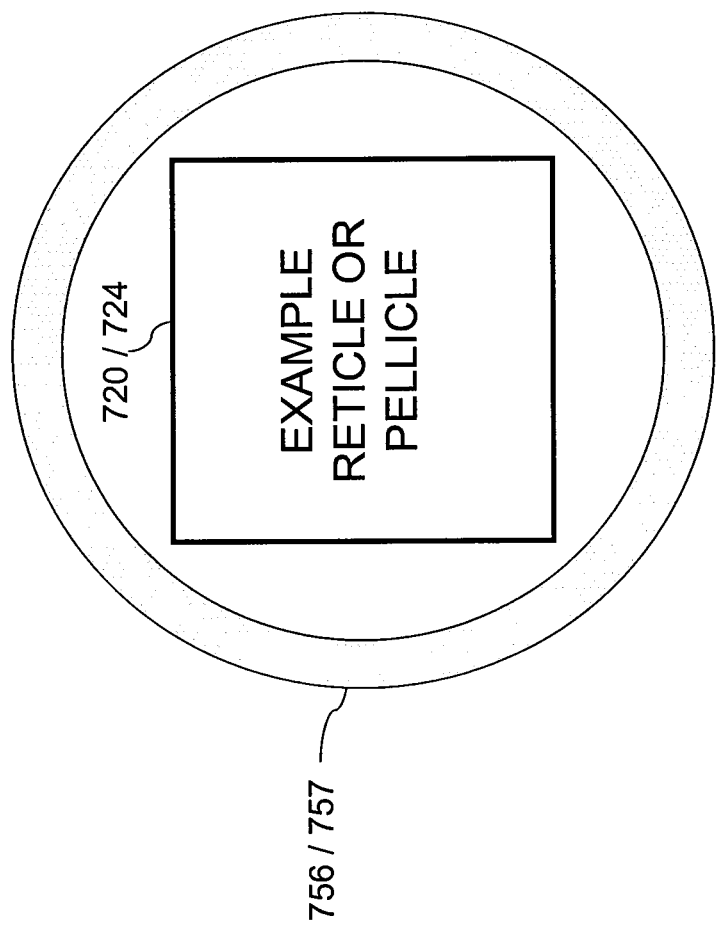
FIGS. 7 and 8 illustrate examples of single illumination sources that can be used with the systems shown in FIGS. 4 and 5, according to embodiments of the present invention.
Figure 8:
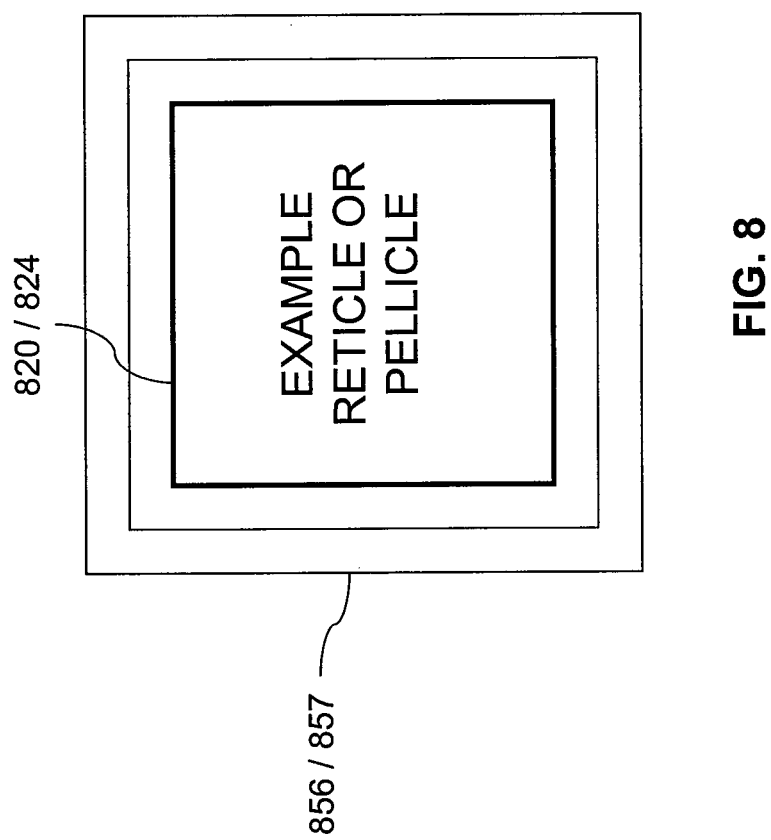

FIG. 4 illustrates a system for inspection of a surface of an object, according to embodiments of the present invention. Specifically, FIG. 4 depicts a system 400 for inspection of a surface of a reticle 420. In FIG. 4, inspection system 454 can be used to assess a surface 421 of reticle 420. Surface 421 as shown in FIG. 4 is a non-patterned surface of reticle 420. However, embodiments of the invention can be used to assess patterned surfaces as well. Inspection system 454 includes one or more illumination sources 456 and a camera system 458 that includes an optical system 462 and a sensor 464. In FIG. 4, two illumination sources 456 are shown. However, any number of illumination sources can be used. For example, four illumination sources can be used, as shown in FIG. 6A, where reticle 620 is illuminated by four illumination sources 656. In another example, six illumination sources can be used, as shown in FIG. 6B, where reticle 620 is illuminated by six illumination sources 656. In a further example, eight illumination sources can be used, as shown in FIG. 6C, where reticle 620 is illuminated by eight illumination sources 656. A single light source of any shape (e.g., a circle, a square, etc.) surrounding a perimeter of reticle 420 could also be used, as shown by a circular light source 756 surrounding a perimeter of reticle 720 in FIG. 7 or by a square light source 856 surrounding a perimeter of reticle 820 in FIG. 8. Illumination sources 456 can be, for example, standard light emitting diodes (LEDs), flash light emitting diodes (flash LEDs), or laser diodes, but are not to be limited to these as other types of illumination sources can also be used.

Referring back to FIG. 4, optical system 462 can include an optic or optics such as one or more lenses, for example. The purpose of optical system 462 is to intercept scattered light from the illuminated reticle surface 421, to project a real image onto sensor 464, and to magnify or de-magnify as necessary. The image is projected from optical system 462 onto sensor 464 as a full field image of reticle surface 421, as shown by lines 472. If reticle surface 421 is too large or if sensor 464 does not have enough capacity for a single projection of a full field image, two or more images can be obtained for an effective full field image. Sensor 464 can be a linear or large area sensor, and can include, but is not to be limited to, a CMOS sensor array or a charge-coupled device (CCD). For example, sensor 464 can include a linear CCD or a large area CCD. There are a variety of linear and large area CCDs currently on the market that can be used in system 400, including CCDs from companies such as Fairchild Imaging of Milpitas, California, Atmel Corporation of San Jose, Calif., and DALSA Corporation of Waterloo, Ontario, Canada. In an embodiment, illumination source or sources 456 may illuminate reticle surface 421 at an oblique angle 470 (e.g., at forty-five degrees or less) so that specular reflection can be prevented from reaching optical system 462 and sensor 464 (in order to avoid optical cross-talk and ghost imaging). In an alternative embodiment, sensor 464 can be placed so as to "look" at reticle surface 421 at an oblique angle, while illumination source 456 can provide normal light. The full field image of reticle surface 421 can be analyzed for particles or other abnormalities, such as particles 476 shown in FIG. 4.

Figure 5:
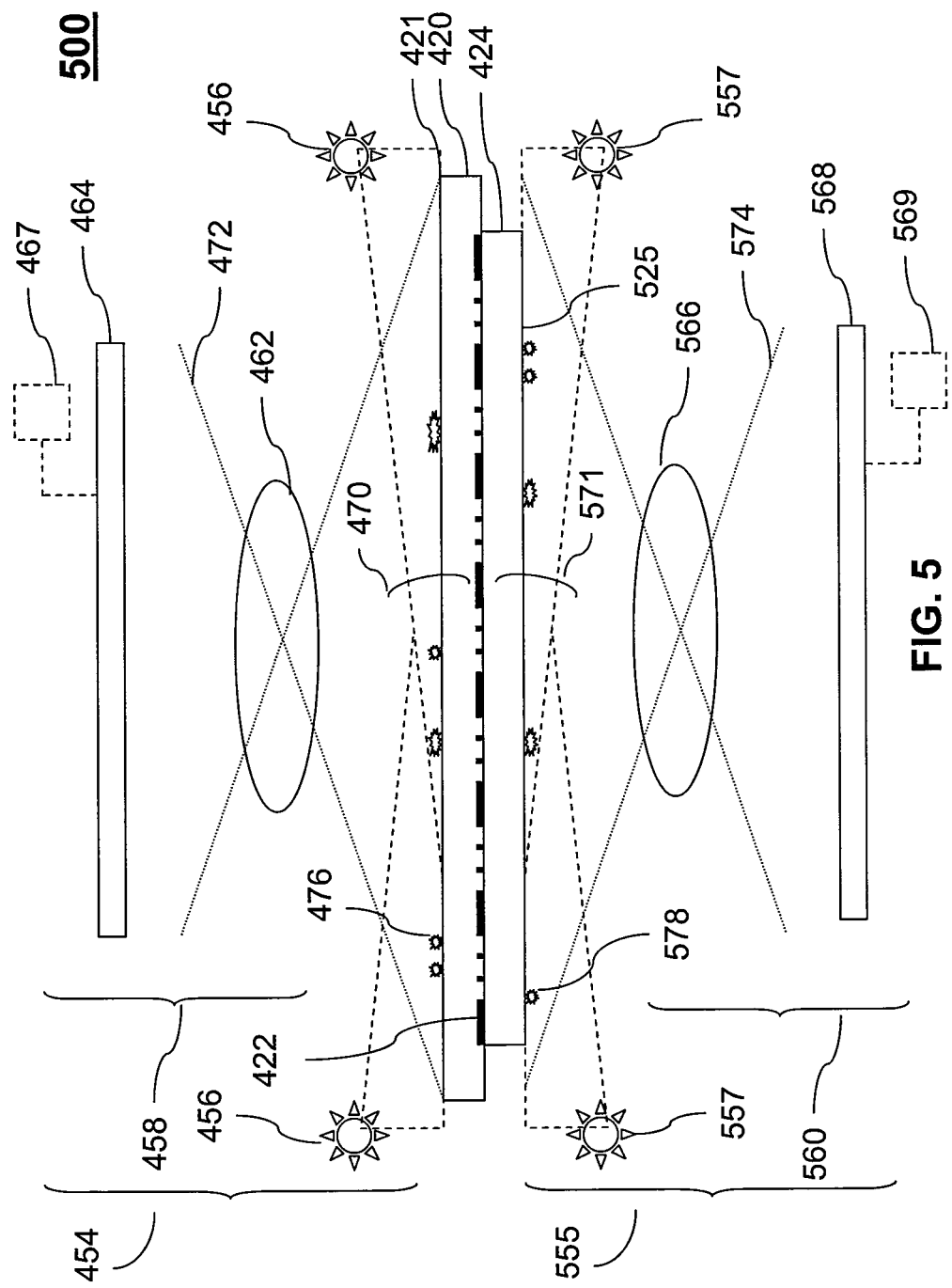
FIG. 5 illustrates a system for inspection of surfaces of multiple objects, according to an embodiment of the present invention.

FIG. 5 depicts a system 500 for inspection of the surfaces of reticle 420 and its associated pellicle 424. In FIG. 5, inspection system 555 can be used to assess a surface 525 of pellicle 424 and is similar to inspection system 454. Inspection system 555 includes one or more illumination sources 557 and a camera system 560 that includes an optical system 566 and a sensor 568. In FIG. 5, two illumination sources 557 are shown. However, as discussed above, any number of illumination sources can be used. For example, four illumination sources can be used, as shown in FIG. 6A, where pellicle 624 is illuminated by four illumination sources 657. In another example, six illumination sources can be used, as shown in FIG. 6B, where pellicle 624 is illuminated by six illumination sources 657. In a further example, eight illumination sources can be used, as shown in FIG. 6C, where pellicle 624 is illuminated by eight illumination sources 657. A single light source of any shape (e.g., a circle, a square, etc.) surrounding a perimeter of pellicle 424 could also be used, as shown by a circular light source 757 surrounding a perimeter of pellicle 724 in FIG. 7 or by a square light source 857 surrounding a perimeter of pellicle 824 in FIG. 8. Illumination sources 557 can be, for example, standard light emitting diodes (LEDs), flash light emitting diodes (flash LEDs), or laser diodes, but are not to be limited to these as other types of illumination sources can also be used.

Referring again to FIG. 5, optical system 566 can include an optic or optics such as one or more lenses, for example. The purpose of optical system 566 is to intercept scattered light from the illuminated pellicle surface 525, to project a real image onto sensor 568, and to magnify or de-magnify as necessary. The image is projected from optical system 566 onto sensor 568 as a full field image of pellicle surface 525, as shown by lines 574. If pellicle surface 525 is too large or if sensor 568 does not have enough capacity for a single projection of a full field image, two or more images can be obtained for an effective full field image. Sensor 568 can be a linear or large area sensor, and can include, but is not to be limited to, a CMOS sensor array or a charge-coupled device (CCD), as discussed earlier. Illumination source or sources 557 may illuminate pellicle surface 525 at an oblique angle 571 (e.g., at forty-five degrees or less) so that specular reflection can be prevented from reaching optical system 566 and sensor 568 (in order to avoid optical cross-talk). In an alternative embodiment, sensor 568 can be placed so as to "look" at pellicle surface 525 at an oblique angle, while illumination source 557 can provide normal light. The full field image of pellicle surface 525 can be analyzed for particles or abnormalities, such as particles 578 shown in FIG. 5.

The optical systems 462/566 may have numerical apertures in the range of, for example, 0.01 to 0.15. A numerical aperture can be chosen to lower depth of focus. For example, a numerical aperture can be chosen such that depth of focus is less than 1/5, or even 1/10, the thickness of reticle 420 (or pellicle 424).

Pellicle 424 can be a lower pellicle, protecting a patterned side of a reticle, or an upper pellicle, protecting a non-patterned side of a reticle. Inspection system 555 can be used to assess a surface of an upper pellicle or a lower pellicle.

As would be appreciated by those skilled in the relevant arts, it is not necessary to include both inspection systems 454 and 555, as one system could be used for inspecting either a surface of reticle 420 (such as shown in FIG. 4) or a surface of pellicle 424, or a surface of both reticle 420 and pellicle 424 but in a serial manner. An advantage of including two inspection systems 454/555 is that assessment of surfaces 421 and 525 can be performed simultaneously, saving valuable time and ultimately resulting in a higher throughput. It is also possible to have more than two inspection systems present (e.g., for other reticle assemblies, wafers, etc., that can be present in a system).

In an embodiment, inspection systems 454/555 can also include respective computer systems 467/569 coupled to respective sensors 464/568, as shown in FIGS. 4 and 5. Computer systems 467 and 569 do not need to be distinct systems, as they can be the same computer system. Computer systems 467/569 can be programmed to analyze full field images obtained from sensors 464/568 to detect particles and/or abnormalities that may be present on the surfaces of reticle 420 and pellicle 424. Computer systems 467 and 569 can also be used to determine sizes and positions of detected particles and/or abnormalities. The determination of particle size and position can be used to reject reticle 420 and/or pellicle 424, for example, if a determined size or position is outside of a predetermined range or other predetermined limits. Using computer systems 467 and 569, systems 400/500 can be programmed to perform inspections using inspection system 454, inspection system 555, both, neither, or even other inspection systems that may be present. In this way, the surface or surfaces to be inspected can be selectable.

In an embodiment, the images projected onto sensors 464 and 568 are full field images of reticle surface 421 and pellicle surface 525, respectively. In an embodiment, these images are high resolution images that allow for detection of real particle shapes and sizes, as well as particle positioning accuracy. High resolution and super high resolution images can be obtained by multi-frame sequential imagery and image enhancement techniques such as sub-pixel resolution processing. They also allow for more accurate rejection of out-of-plane images and optical cross-talk.

The images projected onto sensors 464 and 568 can also be color images. Although real particle sizes and positions are independent of color, multi-colored images can enhance small particle detection. Optical cross-talk images can be caused by diffraction, which is wavelength (or color) dependent. Therefore, multi-color images would allow one to distinguish between true imaging and cross-talk imaging.

Figure 9:
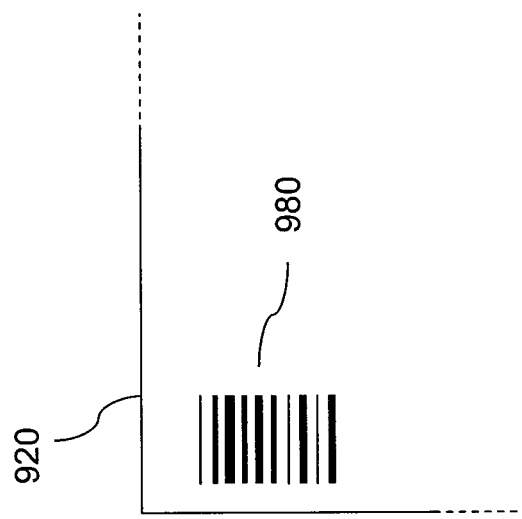
FIG. 9 depicts an example of a one-dimensional bar code located on a surface of an object (e.g., on a reticle).
Figure 10:
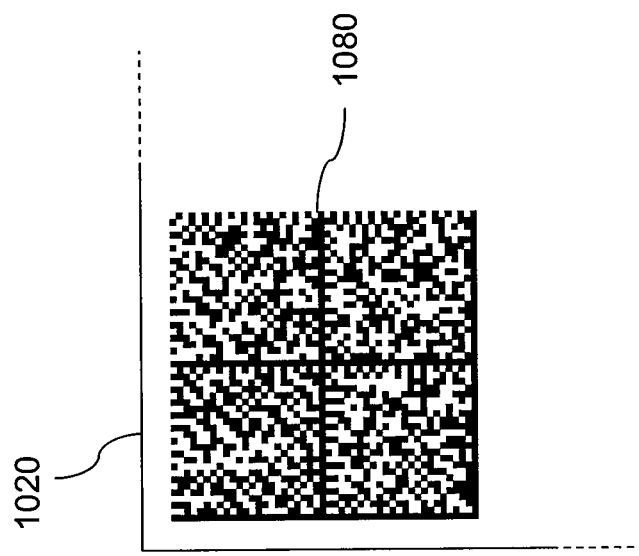
FIG. 10 depicts an example of a two-dimensional bar code located on a surface of an object (e.g., on a reticle).

As described above, a surface inspection system such as system 400/500 is very useful when integrated with a lithography system in which a reticle (or mask) is used. A system such as system 400/500 is especially useful in a lithography system because it can be used to provide many other functions. For example, system 400/500 can be used for metrology purposes. Reticle, and even wafer, pre-alignment can be accomplished by having system 400/500 detect appropriate alignment targets. Reticle (or wafer) identification can be accomplished by reading and interpreting one or more bar codes (e.g., one-dimensional bar codes, two-dimensional bar codes, etc.) located on a reticle (or wafer) surface, such as one-dimensional bar code 980 located on reticle 920 shown in FIG. 9 and two-dimensional bar code 1080 located on reticle 1020 shown in FIG. 10. System 400/500 can also be used to determine the size of a pellicle, detecting whether, for example, the pellicle is too wide. These and other metrology functions can be performed simultaneously with particle detection functions described herein.

Figure 11:
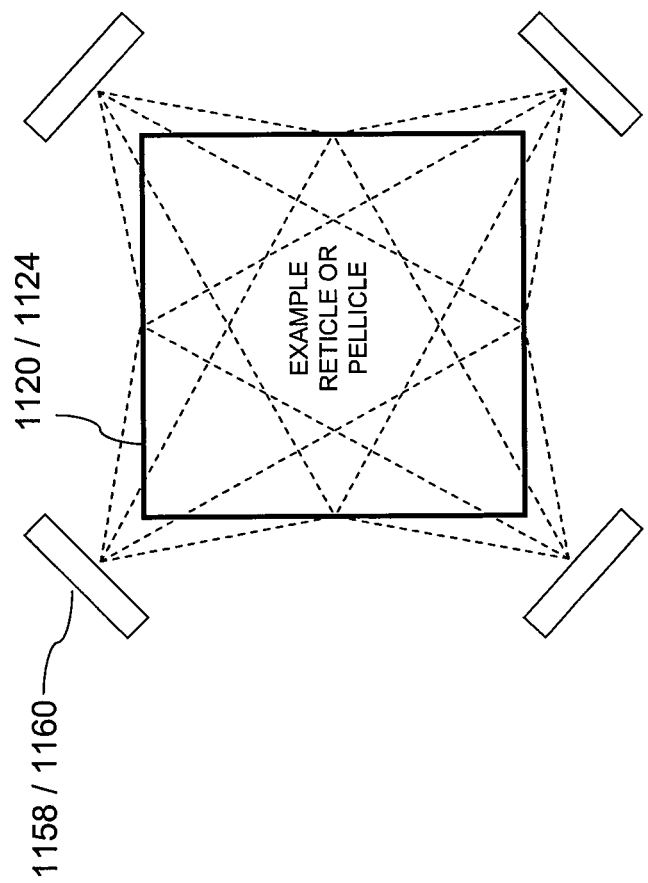
FIG. 11 depicts a stereoscopic (or parallax) imaging system, according to an embodiment of the present invention.

A system such as system 400/500 can also be used with multiple cameras 458/560. Multiple images of at least moderate resolution obtained from multiple cameras can be used to provide improved resolution (super high resolution, or super-resolution) for even further accuracy. Multiple images can also be used to provide stereoscopic, or parallax, imaging. Parallax is the apparent displacement or the difference in apparent direction of an object as seen from two different points that are not co-linear with the object. This can be accomplished using multiple images of the same object from different angles. Stereoscopic, or parallax, imaging can be used to distinguish real particles on an object surface from any optical cross-talk a distance away from the object surface. An example stereoscopic camera configuration is shown in FIG. 11, where multiple cameras 1158/1160 are used to image the surface of reticle 1120 (or pellicle 1124). Although four cameras 1158/1160 are shown, one skilled in the art will understand that a stereoscopic image may be obtained using as few as two cameras.

The above-described additional uses of system 400/500 are only a few examples of how various embodiments and configurations of system 400/500 can be used. Those skilled in the relevant arts will recognize many other uses of system 400/500 after reading the description herein.

Figure 12:
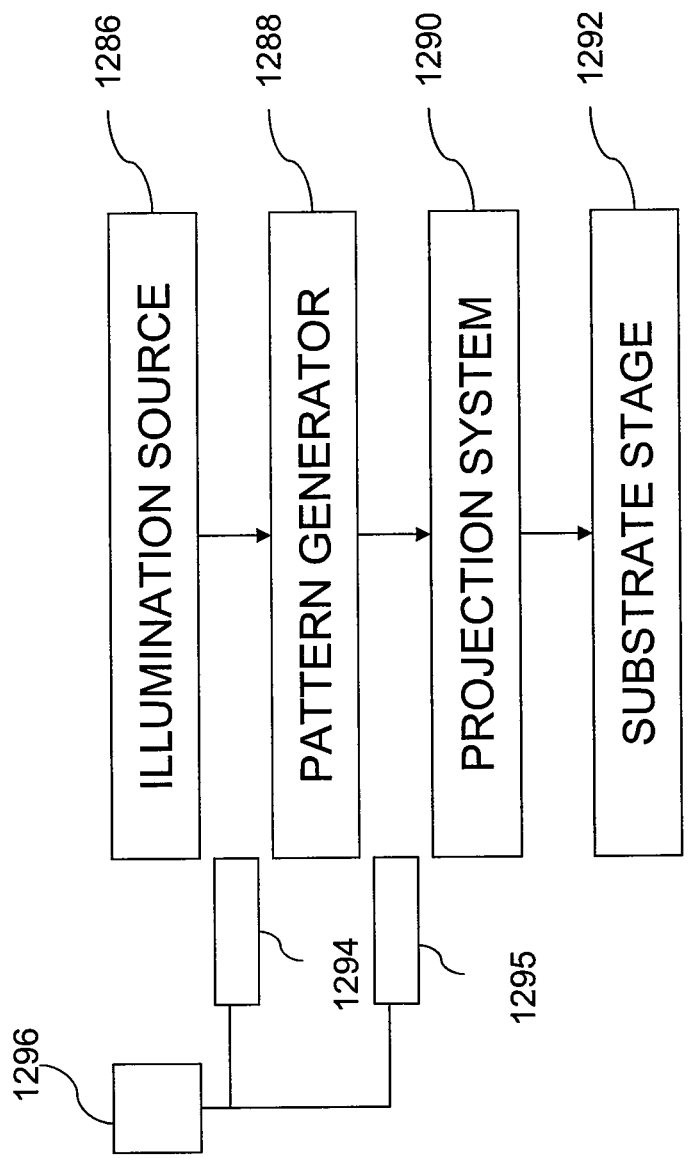
FIG. 12 illustrates an exemplary lithographic system that includes a system for inspection of a surface of an object, such as a reticle and/or pellicle, according to an embodiment of the present invention.

FIG. 12 illustrates an exemplary lithographic system 1200 that includes a system for inspection of a surface of a reticle and/or pellicle, according to an embodiment of the present invention. Lithographic system 1200 includes an illumination source 1286 configured to provide a light beam. Lithographic system 1200 also includes a pattern generator 1288, such as a reticle assembly, configured to pattern the light beam. Lithographic system 1200 further includes a projection system 1290 configured to project the patterned light beam onto a substrate located on a substrate stage 1292. Lithographic system 1200 also includes reticle inspection system 1294 and pellicle inspection system 1295. Reticle inspection system 1294 can be configured similar to inspection system 454 shown and described with reference to FIG. 4. Similarly, pellicle inspection system 1295 can be configured similar to inspection system 555 shown and described with reference to FIG. 5. Reticle inspection system 1294 and pellicle inspection system 1295 are shown coupled to a computer system 1296. Computer system 1296 can have the same functionality as computer systems 467/569, as described earlier with reference to FIGS. 4 and 5. Further examples of lithographic systems in which inspection systems 454 and 555 can be integrated are described below.

A. Example Lithographic Systems

FIGS. 13A and 13B schematically depict lithographic apparatus 1300 and lithographic apparatus 1300', respectively. Lithographic apparatus 1300 and lithographic apparatus 1300' each include: an illumination system (illuminator) IL configured to condition a radiation beam B (e.g., DUV or EUV radiation); a support structure (e.g., a mask table) MT configured to support a patterning device (e.g., a mask, a reticle, or a dynamic patterning device) MA and connected to a first positioner PM configured to accurately position the patterning device MA; and a substrate table (e.g., a wafer table) WT configured to hold a substrate (e.g., a resist coated wafer) W and connected to a second positioner PW configured to accurately position the substrate W. Lithographic apparatuses 1300 and 1300' also have a projection system PS configured to project a pattern imparted to the radiation beam B by patterning device MA onto a target portion (e.g., comprising one or more dies) C of the substrate W. In lithographic apparatus 1300 the patterning device MA and the projection system PS is reflective, and in lithographic apparatus 1300' the patterning device MA and the projection system PS is transmissive.

The illumination system IL may include various types of optical components, such as refractive, reflective, magnetic, electromagnetic, electrostatic or other types of optical components, or any combination thereof, for directing, shaping, or controlling the radiation B.

The support structure MT holds the patterning device MA in a manner that depends on the orientation of the patterning device MA, the design of the lithographic apparatuses 1300 and 1300', and other conditions, such as for example whether or not the patterning device MA is held in a vacuum environment. The support structure MT may use mechanical, vacuum, electrostatic or other clamping techniques to hold the patterning device MA. The support structure MT may be a frame or a table, for example, which may be fixed or movable, as required. The support structure MT may ensure that the patterning device is at a desired position, for example with respect to the projection system PS.

The term "patterning device" MA should be broadly interpreted as referring to any device that may be used to impart a radiation beam B with a pattern in its cross-section, such as to create a pattern in the target portion C of the substrate W. The pattern imparted to the radiation beam B may correspond to a particular functional layer in a device being created in the target portion C, such as an integrated circuit.

The patterning device MA may be transmissive (as in lithographic apparatus 1300' of FIG. 13B) or reflective (as in lithographic apparatus 1300 of FIG. 13A). Examples of patterning devices MA include reticles, masks, programmable mirror arrays, and programmable LCD panels. Masks are well known in lithography, and include mask types such as binary, alternating phase shift, and attenuated phase shift, as well as various hybrid mask types. An example of a programmable mirror array employs a matrix arrangement of small mirrors, each of which may be individually tilted so as to reflect an incoming radiation beam in different directions. The tilted mirrors impart a pattern in the radiation beam B which is reflected by the mirror matrix.

The term "projection system" PS may encompass any type of projection system, including refractive, reflective, catadioptric, magnetic, electromagnetic and electrostatic optical systems, or any combination thereof, as appropriate for the exposure radiation being used, or for other factors, such as the use of an immersion liquid or the use of a vacuum. A vacuum environment may be used for EUV or electron beam radiation since other gases may absorb too much radiation or electrons. A vacuum environment may therefore be provided to the whole beam path with the aid of a vacuum wall and vacuum pumps.

Lithographic apparatus 1300 and/or lithographic apparatus 1300' may be of a type having two (dual stage) or more substrate tables (and/or two or more mask tables) WT. In such "multiple stage" machines the additional substrate tables WT may be used in parallel, or preparatory steps may be carried out on one or more tables while one or more other substrate tables WT are being used for exposure. When the preparatory steps can be performed while one or more other substrate tables WT are being used for exposure, the preparatory steps are said to occur during an "in-line phase" because the preparatory steps are performed within the desired throughput of the lithographic apparatus 1300 and/or lithographic apparatus 1300'. In contrast, when the preparatory steps cannot be performed while one or more other substrate tables WT are being used for exposure, the preparatory steps are said to occur during an "off-line phase" because the preparatory steps cannot be performed within a desired throughput of lithographic apparatus 1300 and/or lithographic apparatus 1300'. As described in more detail herein, inspecting the surfaces of a reticle (or mask) and/or a pellicle may be performed in an off-line phase, an in-line phase, or a combination thereof.

Referring to FIGS. 13A and 13B, the illuminator IL receives a radiation beam from a radiation source SO. The source SO and the lithographic apparatuses 1300, 1300' may be separate entities, for example when the source SO is an excimer laser, such as an ArF excimer laser. In such cases, the source SO is not considered to form part of the lithographic apparatuses 1300 or 1300', and the radiation beam B passes from the source SO to the illuminator IL with the aid of a beam delivery system BD (FIG. 13B) comprising, for example, suitable directing mirrors and/or a beam expander. In other cases, the source SO may be an integral part of the lithographic apparatuses 1300, 1300'—for example when the source SO is a mercury lamp. The source SO and the illuminator IL, together with the beam delivery system BD, if required, may be referred to as a radiation system.

The illuminator IL may comprise an adjuster AD (FIG. 13B) for adjusting the angular intensity distribution of the radiation beam. Generally, at least the outer and/or inner radial extent (commonly referred to as σ-outer and σ-inner, respectively) of the intensity distribution in a pupil plane of the illuminator may be adjusted. In addition, the illuminator IL may comprise various other components (FIG. 13B), such as an integrator IN and a condenser CO. The illuminator IL may be used to condition the radiation beam B, to have a desired uniformity and intensity distribution in its cross section.

Referring to FIG. 13A, the radiation beam B is incident on the patterning device (e.g., mask) MA, which is held on the support structure (e.g., mask table) MT, and is patterned by the patterning device MA. In lithographic apparatus 1300, the radiation beam B is reflected from the patterning device (e.g., mask) MA. After being reflected from the patterning device (e.g., mask) MA, the radiation beam B passes through the projection system PS, which focuses the radiation beam B onto a target portion C of the substrate W. With the aid of the second positioner PW and position sensor IF2 (e.g., an interferometric device, linear encoder or capacitive sensor), the substrate table WT may be moved accurately, e.g. so as to position different target portions C in the path of the radiation beam B. Similarly, the first positioner PM and another position sensor IF1 may be used to accurately position the patterning device (e.g., mask) MA with respect to the path of the radiation beam B. Patterning device (e.g., mask) MA and substrate W may be aligned using mask alignment marks M1, M2 and substrate alignment marks P1, P2. As described elsewhere herein, embodiments of the present invention can be used to locate, read, and/or interpret these alignment marks.

Referring to FIG. 13B, the radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF (e.g., an interferometric device, linear encoder or capacitive sensor), the substrate table WT can be moved accurately, e.g. so as to position different target portions C in the path of the radiation beam B. Similarly, the first positioner PM and another position sensor (which is not explicitly depicted in FIG. 13B) can be used to accurately position the mask MA with respect to the path of the radiation beam B, e.g., after mechanical retrieval from a mask library, or during a scan.

In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (known as scribe-lane alignment marks). Similarly, in situations in which more than one die is provided on the mask MA, the mask alignment marks may be located between the dies.

The lithographic apparatuses 1300 and 1300' may be used in at least one of the following modes:

1. In step mode, the support structure (e.g., mask table) MT and the substrate table WT are kept essentially stationary, while an entire pattern imparted to the radiation beam B is projected onto a target portion C at one time (i.e., a single static exposure). The substrate table WT is then shifted in the X and/or Y direction so that a different target portion C may be exposed.

2. In scan mode, the support structure (e.g., mask table) MT and the substrate table WT are scanned synchronously while a pattern imparted to the radiation beam B is projected onto a target portion C (i.e., a single dynamic exposure). The velocity and direction of the substrate table WT relative to the support structure (e.g., mask table) MT may be determined by the (de-)magnification and image reversal characteristics of the projection system PS.

3. In another mode, the support structure (e.g., mask table) MT is kept substantially stationary holding a programmable patterning device, and the substrate table WT is moved or scanned while a pattern imparted to the radiation beam B is projected onto a target portion C. A pulsed radiation source SO may be employed and the programmable patterning device is updated as required after each movement of the substrate table WT or in between successive radiation pulses during a scan. This mode of operation may be readily applied to maskless lithography that utilizes programmable patterning device, such as a programmable mirror array of a type as referred to herein.

Combinations and/or variations on the described modes of use or entirely different modes of use may also be employed.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion," respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

The terms "radiation" and "beam" used herein encompass all types of electromagnetic radiation, including ultraviolet (UV) radiation (e.g., having a wavelength of or about 365, 248, 193, 157 or 126 nm) or extreme ultraviolet radiation (e.g., having a wavelength of 5 nm or above).

The terms "lens" and "optic," where the context allows, may refer to any one or combination of various types of optical components, including refractive and reflective optical components.

B. Example Computer System

Embodiments of the present invention may be implemented using hardware, software or a combination thereof, and may be implemented in one or more computer systems or other processing systems. An example of a computer system 2400 is shown in FIG. 24. Computer system 2400 can also be used as computer systems 467, 569, and/or 1296, as described above.

The computer system 2400 includes one or more processors, such as processor 2404. Processor 2404 may be a general purpose processor (such as, a CPU) or a special purpose processor (such as, a GPU). Processor 2404 is connected to a communication infrastructure 2406 (e.g., a communications bus, cross-over bar, or network). Various software embodiments can be described in terms of this exemplary computer system. After reading this description, it will become apparent to a person skilled in the relevant art(s) how to implement the invention using other computer systems and/or architectures.

Computer system 2400 (optionally) includes a display interface 2402 that forwards graphics, text, and other data from communication infrastructure 2406 (or from a frame buffer not shown) for display on display unit 2430.

Computer system 2400 also includes a main memory 2408, preferably random access memory (RAM), and may also include a secondary memory 2410. The secondary memory 2410 may include, for example, a hard disk drive 2412 and/or a removable storage drive 2414, representing a floppy disk drive, a magnetic tape drive, an optical disk drive, etc. The removable storage drive 2414 reads from and/or writes to a removable storage unit 2418 in a well known manner. Removable storage unit 2418 represents a floppy disk, magnetic tape, optical disk, etc. which is read by and written to by removable storage drive 2414. As will be appreciated, the removable storage unit 2418 includes a computer-readable storage medium having stored therein computer software and/or data.

In alternative embodiments, secondary memory 2410 may include other similar devices for allowing computer programs or other instructions to be loaded into computer system 2400. Such devices may include, for example, a removable storage unit 2422 and an interface 2420. Examples of such may include a program cartridge and cartridge interface, a removable memory chip (such as an erasable programmable read only memory (EPROM), or programmable read only memory (PROM)) and associated socket, and other removable storage units 2422 and interfaces 2420, which allow software and data to be transferred from the removable storage unit 2422 to computer system 2400.

Computer system 2400 may also include a communications interface 2424. Communications interface 2424 allows software and data to be transferred between computer system 2400 and external devices. Examples of communications interface 2424 may include a modem, a network interface (such as an Ethernet card), a communications port, a Personal Computer Memory Card International Association (PCMCIA) slot and card, etc. Software and data transferred via communications interface 2424 are in the form of signals 2428 which may be electronic, electromagnetic, optical or other signals capable of being received by communications interface 2424. These signals 2428 are provided to communications interface 2424 via a communications path (e.g., channel) 2426. This channel 2426 carries signals 2428 and may be implemented using wire or cable, fiber optics, a telephone line, a cellular link, an radio frequency (RF) link and other communications channels.

In this document, the terms "computer program medium" and "computer-readable storage medium" are used to generally refer to media such as removable storage drive 2414 and a hard disk installed in hard disk drive 2412. These computer program products provide software to computer system 2400.

Computer programs (also referred to as computer control logic) are stored in main memory 2408 and/or secondary memory 2410. Computer programs may also be received via communications interface 2424. Such computer programs, when executed, enable the computer system 2400 to perform features of the present invention, such as analyzing a surface of an object as discussed herein. In particular, the computer programs, when executed, can enable the processor 2404 to perform the features of the present invention, including the implementation of the methods illustrated in FIGS. 14-23 discussed herein. Accordingly, such computer programs represent controllers of the computer system 2400.

III. Example Methods for Surface Inspection

FIG. 14 depicts a flow diagram illustrating an example method 1400 of inspecting a surface of an object, such as a reticle or pellicle, in accordance with an embodiment of the present invention. Method 1400 begins at step 1402. In step 1402, a surface of an object (e.g., a reticle, a pellicle, etc.) is illuminated with an illumination beam. In an embodiment, the illumination beam is provided to the object surface at an oblique angle. In step 1404, scattered light from the illuminated object surface is intercepted. In step 1406, a real image of a desired area of the object surface is projected onto a sensor (e.g., sensor 464 or 568 of FIGS. 4 and 5). In an embodiment, the sensor "looks" at the object surface at an oblique angle, while the illumination beam can provide normal light. In step 1408, the real image is processed to detect particles located on the object surface. For example, a computer system (e.g., computer systems 467, 569, or 1296) coupled to the sensor can be used to analyze the real image for particle detection. The method then ends.

FIG. 15 is a flowchart depicting an optional further step of method 1400, according to an embodiment of the present invention. In step 1502, particle sizes and positions of detected particles are determined. This information can be used to make decisions regarding use of the object being assessed. For example, a decision may need to be made whether the object needs to be rejected based on whether the determined particle sizes and positions are within predetermined ranges or other limits.

FIG. 16 is a flowchart depicting an optional further step of method 1400, according to an embodiment of the present invention. Step 1602 stems from step 1406. In step 1602, the real images are focused. For example, an optical system, such as optical systems 462 or 466 shown in FIG. 4, can focus the image being projected. Method 1400 continues at step 1408.

FIG. 17 is a flow diagram illustrating an example method 1700 of manufacturing of a device, in accordance with an embodiment of the present invention. Method 1700 begins at step 1702. In step 1702, a surface of a reticle is assessed for particles. This assessment can be performed using method 1400 described above. In step 1704, an illumination beam is produced. In step 1706, the reticle is illuminated with the illumination beam. In step 1708, a pattern of the illumination beam is generated from the reticle. In step 1710, the patterned illumination beam is projected onto a target portion of a substrate. Method 1700 then ends.

FIG. 18 is a flowchart depicting an optional further step of method 1700, according to an embodiment of the present invention. Step 1802 stems from step 1702. In step 1802, the reticle is rejected if one or more of determined particle sizes and positions fall outside of corresponding predetermined ranges or limits. For example, the reticle may be rejected if particles are larger than a predetermined size limit or located at a critical position on the reticle. If the reticle is rejected, the method then ends so that the reticle can be replaced, for example. If the reticle is not rejected, method 1700 continues at step 1704.

FIG. 19 is a flowchart depicting an optional further step of method 1700, according to an embodiment of the present invention. Step 1902 stems from step 1710. In step 1902, assessing step 1702 is repeated at predetermined breaks or intervals during lithographic processing. Because particles may appear, or crystallization may occur, on a reticle at any time, it is important to re-assess the reticle surface at one or more breaks or predetermined intervals during lithographic processing.

FIG. 20 is a flow diagram illustrating an example method 2000 of manufacturing of a device, in accordance with an embodiment of the present invention. Method 2000 begins at step 2002. In step 2002, a surface of a reticle is assessed for particles. In step 2004, a surface of a pellicle associated with the reticle is assessed for particles. Each of these assessments can be performed using method 1400 described above. In step 2006, an illumination beam is produced. In step 2008, the reticle is illuminated with the illumination beam. In step 2010, a pattern of the illumination beam is generated from the reticle. In step 2012, the patterned illumination beam is projected onto a target portion of a substrate. Method 2000 then ends.

FIG. 21 is a flowchart depicting an optional further step of method 2000, according to an embodiment of the present invention. Step 2102 stems from step 2004. In step 2102, the reticle and its associated pellicle are rejected if one or more of determined particle sizes and positions fall outside of corresponding predetermined ranges or limits. For example, the reticle assembly may be rejected if particles are larger than a predetermined size limit or located at a critical position. If the reticle assembly is rejected, the method then ends so that the reticle assembly can be replaced, for example. If the reticle assembly is not rejected, method 2000 continues at step 2006.

FIG. 22 is a flowchart depicting an optional further step of method 2000, according to an embodiment of the present invention. Step 2202 stems from step 2012. In step 2202, assessing steps 2002 and 2004 are repeated at predetermined breaks or intervals during lithographic processing. Because particles may appear, or crystallization may occur, at any time, it is important to re-assess the reticle and pellicle surfaces at one or more breaks or predetermined intervals during lithographic processing.

FIG. 23 is a flowchart depicting an optional further step within step 2004. In step 2302, the surface of the pellicle is assessed simultaneously with the assessment of the surface of the reticle. Method 2000 then continues at step 2006. When the surfaces of the reticle and pellicle are inspected simultaneously, considerable time is saved, and throughput is ultimately increased.

IV. Features and Advantages

Some of the features and advantages of the various embodiments will now be described. Compared to conventional techniques for surface inspection, such as the probe beam technique, which conducts serial surface scanning of probe beam spots sized at about 200 µm with particle size approximations based on intensity, embodiments of the invention presented herein have many advantages. Embodiments of the present invention use real imaging, which allows a direct measurement of particle sizes. In embodiments, a higher numerical aperture provides a lower depth-of-focus, higher resolution, and thus, more appropriate determinations of reticle rejection. Because simultaneous surface scanning of a reticle surface and the surface of its associated pellicle may be achieved, inspection time is greatly reduced, resulting in higher throughput. Furthermore, as discussed above, embodiments of this invention can be used for various other functions, such as metrology uses (e.g., reticle or wafer pre-alignment, bar code reading, pellicle size detection, etc.) and multi-camera uses (e.g., improved (super) resolution, stereoscopic (parallax) imaging, etc.). Embodiments of the invention also allow for fixed and movable reticle tables.

V. Conclusion

Described above are embodiments related to particle detection on a surface of an object. It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc.

Although specific reference may have been made above to the use of embodiments of the invention in the context of optical lithography, it will be appreciated that the invention may be used in other applications, for example imprint lithography, and where the context allows, is not limited to optical lithography.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams. In addition, visible and infrared radiation can be used for illuminating reticle inspection systems.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

What is claimed is:

1. A system for inspecting a surface of an object, comprising:
    an illumination source configured to provide an illumination beam to illuminate the surface of the object;
    an optic, having a numerical aperture corresponding to a depth of focus less than ⅕ of a thickness of the object, and configured to intercept scattered light from the illuminated object surface and project a substantially full field real image of the object surface;
    a sensor configured to receive the projected real image; and
    a computer system configured to analyze the real image to detect solid particles located on the object surface.

2. The system of claim 1, wherein the object is a reticle.

3. The system of claim 2, wherein the surface is a non-patterned side of the reticle.

4. The system of claim 1, wherein the object is a pellicle associated with a reticle.

5. The system of claim 1, wherein the illumination source is configured such that the illumination beam impinges on the object surface at an oblique angle.

6. The system of claim 1, wherein the illumination source is configured such that the illumination beam impinges on the object in a generally normal direction, and the sensor is placed so as to receive scattered light from the surface at an oblique angle.

7. The system of claim 1, wherein the optic and the sensor form a camera, two or more cameras are placed facing the object surface from different angles, real images are obtained from the two or more cameras and the object surface is parallax imaged by the two or more cameras.

8. The system of claim 1, wherein the at least one illumination source, the optic, and the sensor are integrated into a lithography system for enabling the system to perform in-situ inspection of a pellicized reticle.

9. A lithography system, comprising:
a particle detection system having
a first illumination source configured to provide an illumination beam to illuminate a surface of an object;
an optic, having a numerical aperture corresponding to a depth of focus less than $\frac{1}{5}$ of a thickness of the object, and configured to intercept scattered light from an illuminated object surface and project a substantially full field real image of the object surface; and
a sensor for receiving the projected real image, whereby particles located on the object surface are detectable in the real image;
a second illumination source configured to provide a light beam to the object; and
a projection system configured to project a patterned light beam from the object onto a substrate.

10. The system of claim 9, wherein the object is the reticle.

11. The system of claim 9, wherein the object is a pellicle associated with the reticle.

12. The system of claim 9, wherein the real image includes a detectable bar code.

13. A method of device manufacturing comprising:
assessing a surface of a reticle for particles, including producing a first illumination beam;
illuminating the reticle surface with the first illumination beam;
intercepting scattered light from the illuminated reticle surface using an optic having a numerical aperture corresponding to a depth of focus less than $\frac{1}{5}$ of a thickness of the object;
projecting a substantially full field real image of the reticle surface onto a sensor; and
processing the real image to detect particles located on the reticle surface;
producing a second illumination beam;
illuminating the reticle with the second illumination beam;
generating a pattern of the second illumination beam from the reticle; and
projecting the patterned second illumination beam onto a target portion of a substrate.

14. An in-situ contaminant detection system, comprising:
an optic with a predefined numerical aperture that lowers depth of focus to be less than $\frac{1}{5}$ of a thickness of a patterned object, wherein the optic is disposed in a lithography system and configured to:
receive scattered light from a surface of the patterned object that is being illuminated for obtaining a two-dimensional image of the surface under inspection, and
project a substantially hill field real image of the surface of the illuminated object; and
a sensor configured to receive the projected real image for inspecting the surface of the illuminated object for a presence of any solid particles thereon.

15. The system of claim 14, wherein the object is a reticle.

16. The system of claim 15, wherein the surface is a non-patterned side of the reticle.

17. The system of claim 14, wherein the object is a pellicle associated with a reticle.

18. The system of claim 14, wherein an illumination beam impinges on the surface of the object at an oblique angle.

19. The system of claim 14, wherein the optic and the sensor form a camera, two or more cameras being placed facing the surface of the object from different angles, wherein real images of the surface of the object and obtained from the two or more cameras are parallax imaged by the two or more cameras.

20. The system of claim 14, wherein at least one illumination source, the optic, and the sensor are integrated into the lithography system and are configured to perform in-situ inspection of a pellicized reticle.

* * * * *

UNITED STATES PATENT AND TRADEMARK OFFICE
CERTIFICATE OF CORRECTION

PATENT NO. : 8,634,054 B2
APPLICATION NO. : 12/537728
DATED : January 21, 2014
INVENTOR(S) : Vladimirsky et al.

Page 1 of 1

It is certified that error appears in the above-identified patent and that said Letters Patent is hereby corrected as shown below:

In the Claims

In Column 18, claim 14, line 21, please delete "hill" and insert --full--

Signed and Sealed this
First Day of July, 2014

Michelle K. Lee
*Deputy Director of the United States Patent and Trademark Office*